United States Patent [19]

Sugihara et al.

[11] Patent Number: 4,937,246

[45] Date of Patent: Jun. 26, 1990

[54] PAF ANTAGONIST, 1,4-DISUBSTITUTED PIPERAZINE COMPOUNDS AND PRODUCTION THEREOF

[75] Inventors: Hirosada Sugihara; Katsumi Itoh, both of Osaka; Kohei Nishikawa, Kyoto, all of Japan

[73] Assignee: Takeda Chemical Industries, Ltd., Osaka, Japan

[21] Appl. No.: 274,975

[22] Filed: Nov. 22, 1988

[30] Foreign Application Priority Data

Nov. 25, 1987 [DE] Fed. Rep. of Germany ......... 296887

[51] Int. Cl.⁵ .................. A61K 31/495; A61K 31/50; C07D 295/18

[52] U.S. Cl. .................................... 514/255; 514/252; 544/376

[58] Field of Search ................. 514/255, 252; 544/376

[56] References Cited

U.S. PATENT DOCUMENTS 4,148,897  4/1979  Oka et al. ............................ 514/255
4,221,793  9/1980  Weber et al. ........................ 544/376
4,556,656 12/1985  McCall ................................ 544/376

FOREIGN PATENT DOCUMENTS 0284359  9/1988  European Pat. Off. ............ 544/171

OTHER PUBLICATIONS

Chemical Abstracts, American Chemical Society, vol. 59, (1963).
Chemical Abstracts, American Chemical Society, vol. 79, (1973).
Chemical Abstracts, American Chemical Society, vol. 88, (1978).
Chemical Patents Index, "Basic Abstracts Journal", Sect. B, Derwent Publications Ltd., London (Sep. 3, 1986).
Chemical Patents Index, "Basic Abstracts Journal", Sect. B, Derwent Publications Ltd., London (Mar. 18, 1987).
Itoh, Katsumi et al., "Synthesis and Biological Activities of 3-Aminomethyl-1,2-Dihydronaphthalene Derivatives", Chem. Pharm. Bull., vol. 31(6), pp. 2006-2015 (1963).
Terashita, Zen-ichi et al., "A Specific Antagonist of Platelet Activating Factor (PAF)", Life Sciences, vol. 32, pp. 1975-1982, Apr. 25, 1983.
Purcell, William P. et al., "Application of Regression Analyses to Antitumor Activities of Various Acetylenic Caramates", Journal of Medicinal Chemistry, vol. 11, No. 2, Feb. 1968.
European Serch Report Corresponding to EP 85 10 8942, (1978).
Chemical Abstracts, American Chemical Society, vol. 66 (1967).
Chemical Abstracts, American Chemical Society, vol. 69 (1968).
Chemical Abstracts, American Chemical Society, vol. 78 (1973).
Chemical Abstracts, American Chemical Society, vol. 87 (1977).
Chemical Abstracts, American Chemical Society, vol. 110 (1989).

*Primary Examiner*—Douglas W. Robinson
*Assistant Examiner*—Kevin E. Weddington
*Attorney, Agent, or Firm*—Wegner & Bretschneider

[57] ABSTRACT

Platelet Activating Factor (PAF) antagonists which comprise the compounds of the formula (I):

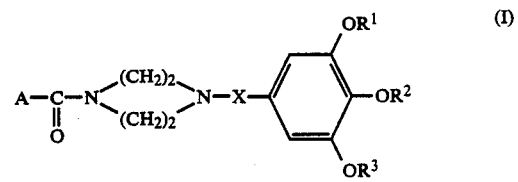

wherein A is an optionally substituted phenyl or an optionally substituted heterocyclic group; X is methylene group, carbonyl group or thiocarbonyl group; $R^1$, $R^2$ and $R^3$ are independently a lower alkyl group, and their salts are excellent in absorption from the intestinal canal.

Among the compounds of the formula (I), those wherein A is an optionally substituted 2,3-dihydro-1-benzoxepin-4-yl group are novel compounds and exhibit excellent PAF antagonism.

14 Claims, No Drawings

PAF ANTAGONIST, 1,4-DISUBSTITUTED PIPERAZINE COMPOUNDS AND PRODUCTION THEREOF

BACKGROUND OF THE INVENTION

This invention relates to PAF antagonists (platelet activating factor antagonists). More specifically stating, the present invention relates to a PAF antagonist containing a compound of the formula (I):

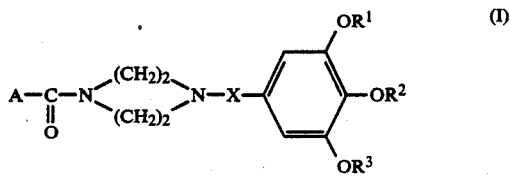

[wherein A stands for an optionally substituted phenyl group or an optionally substituted heterocyclic group; X stands for a methylene group (—$CH_2$—), carbonyl group (—CO—) or thiocarbonyl group (—CS—); $R^1$, $R^2$ and $R^3$ each stand for a lower alkyl group] or a salt thereof.

This invention also relates to a novel 1,4-disubstituted piperazine compound of the formula (I) [wherein A stands for an optionally substituted 2,3-dihydro-1-benzosepin-4-yl group; X, $R^1$, $R^2$ and $R^3$ are of the same meaning as defined above] or a salt thereof, which is useful as a PAF antagonist, and production thereof.

PAF has a phospholipid structure and is a chemical transmitter existing in a living body. It has been made clear that PAF is, in a living body, closely concerned with allergy, anaphylaxis, inflammation, etc., and it has also been known that PAF has a strong hypotensive activity and platelet agglutinating activity. On administering PAF to an animal, the animal may in some cases be killed from shock. Symptoms caused by the shock from PAF have much resemblance to those caused by the shock from endotoxin, and it has been considered that PAF is concerned with the endotoxin shock.

On the other hand, while a variety of compounds having PAF-antagonistic activity have been known, very few of them are satisfactory in PAF-antagonistic activity in a living body. And, even when the PAF antagonistic activity in a living body is satisfactory, not a few of those compounds have some restrictions in the administration method.

DETAILED DESCRIPTION

The object of the present invention is to provide a PAF-antagonistic agent containing a compound represented by the above-mentioned formula (I).

Referring to the formula (I), examples of the heterocyclic groups shown by A include monocyclic, bicyclic or tricyclic heterocyclic groups which may optionally be saturated partially. Examples of the monocyclic heterocyclic groups include 5- to 8-membered heterocyclic groups containing 1 to 3 hetero-atoms selected from nitrogen, oxygen and sulfur, more specifically, pyridyl (2-pyridyl, 3-pyridyl, 4-pyridyl), thienyl (2-thienyl, 3-thienyl), furyl, thiazolyl (2-thiazolyl, etc.) etc.

Examples of the bicyclic heterocyclic groups which may optionally be saturated partially include condensed bicyclic heterocyclic groups formed by condensation of benzene ring and 5- to 8-membered hetero-ring containing 1 to 3 hetero-atoms selected from nitrogen, oxygen and sulfur, more specifically, quinolyl (2-quinolyl, 3-quinolyl, 4-quinolyl, 5-quinolyl, 6-quinolyl, 7quinolyl), isoquinolyl (3-isoquinolyl, etc.), indolyl (5-indolyl, etc.), benzothiazolyl (2-benzothiazolyl, etc.), 1,3-benzodioxolyl (1,3-benzodioxol-5-yl, etc.), benzofuranyl (2-benzofuranyl, etc.), 2,3-dihydrobenzofuranyl, benzopyranyl (2-benzopyranyl, 3-benzopyranyl, etc., 3,4dihydrobenzopyranyl, 1-benzoxepinyl (1-benzoxepin-4-yl, 1-benzoxepin-8-yl, etc.), 2,3-dihdyro-1-benzoxepinyl (2,3- dihydro-1-benzoxepin-4-yl, etc.), 2,3,4,5-tetrahydro-1-benzoxepinyl, 1-benzothiepinyl, 2,3-dihdyro-1-benzothiepinyl (2,3- dihydro-1-benzothiepin-4-yl, etc.), 2,3,4,5-tetrahydro-1benzothiepinyl, 3,4-dihydro-2H-1,5-benzoxepinyl, 2,3-dihydro1,4-benzodioxynyl[1,4-benzodioxanyl](2,3-dihydro-1,4-benzodioxin-6-yl, etc.), chromenyl (2H-chromen-3-yl, etc.), chromanyl (3-chromanyl, etc.), etc.

Examples of the tricyclic heterocyclic groups which may be saturated partially include condensed tricyclic heterocyclic groups formed by condensation of (i) 5- to 8-membered hetero-ring containing 1 to 3 hetero-atoms selected from nitrogen, oxygen and sulfur, (ii) benzene ring and (iii) benzene ring, 3- to 8-membered cycloalkane, 4- to 8-membered cycloalkene or 5- to 8-membered hetero-ring containing 1 to 3 hetero-atoms selected from nitrogen, oxygen and sulfur, and spiroheterocyclic group formed by condensation of spirounion of 3- to -b 8-membered cloalkane to a condensed ring of (i) and (ii), etc., more specifically, dibenzofuranyl (2-dibenzofuranyl, etc.), 3,4-dihydrodibenzofuranyl (3,4-dihydrodibenzofuran-2-yl, etc.), 1,2,3,4-tetrahydrodibenzofuranyl, dibenzothiophenyl (2-dibenzothiophenyl, etc.), 3,4-dihydrodibenzothiophenyl (3,4-dihydrobenzothiophen2-yl, etc.), 1,2,3,4-tetrahydrobidenzothiophenyl(1,2,3,4-tetrahydrobenzothiophen-2-yl, etc.), naphtho[2,3-d]-1,3-dioxolyl, 5,6-dihydronaphtho[2,3-d]-1,3-dioxolyl (5,6-dihydronaphtho[2,3-d]-1,3-dioxol-7-yl, etc.), 5,6,7,8-tetrahydronaphtho[2,3-d]-1,3-dioxolyl, naphtho[2,3-b]-1,4-dioxanyl, 6,7-dihydronaphtho[2,3-b]-1,4-dioxanyl (6,7-dihydronaphtho[2,3-b]-1,4-dioxan-8-yl, etc.), 5H-1,4-cyclohepta[f]-1,3-benzodioxolyl, 6,7-dihydro-5H-cyclohepta[f]-1,3-benzoxolyl (6,7-dihydro-5H-cyclohepta[f]-1,3-benzodioxol-8-yl, etc.), 6H-cyclohepta[g]-1,4-benzodioxanyl, 7,8-dihydro-6H-cyclohepta[g]-1,4-benzodioxanyl (7,8-dihydro6H-cyclohepta[g]-1,4-benzodioxan-9-yl, etc.), dibenzo-p-dioxynyl, xanthenyl, 1,2-dihydroxanthenyl, naphtho[2,1-b]furanyl, 1,2,8,9-tetrahydronaphtho[2,1-b]furnayl, 2,3,5,6tetrahydronaphtho[2,1-b]furanyl, spiro[benzofuran-2(3H), 1'-cyclopropane]-yl (spiro[benzofuran-2(3H), 1'-cyclopropane]5-yl, etc.), etc.

The phenyl group or heterocyclic groups shown by the above-mentioned A include those having one or more (preferably not more than 4) substituents such as, among others, a lower alkyl group, a halo lower alkyl group, a hydroxy lower alkyl group, an acyloxy lower alkyl group, a lower alkoxy lower alkyl group, a lower alkoxy group, a halo lower alkoxy group, a lower alkoxy carbonyl lower alkoxy group, a lower alkenyloxy group, aralkyloxy group, a lower alkoxy lower alkoxy group, a lower alkoxycarbonyl group, carboxyl group, carbamoyl group, an N,N-di-lower alkylcarbamoyl group, an N-lower alkyl carbamoyl group, halo group, cyano group, nitro group, hydroxy group, acyloxy group, amino group, a lower alkylsulfonylamino group, acylamino group, a lower alkoxycarbonylamino group, acyl group, mercapto group, a lower alkylthio group, a lower alkylsulfinyl group, a lower alkylsulfonyl group and oxo group. Among these substituents, a lower alkyl group, a lower alkoxy group and oxo group are more preferable. When the phenyl group or heterocyclic groups have two or more substituents, the kinds of these substituents may be the same or different from one another.

Lower alkyl groups as the above-mentioned substituents are exemplified by alkyl groups whose carbon number ranges from about 1 to about 4, such as methyl, ethyl, propyl, isopropyl, butyl, isobutyl, sec-butyl, tert-butyl, etc. As the halo lower alkyl group, mention is made of alkyl groups whose carbon number ranges from about 1 to about 4, which are substituted with 1 to 3 halo groups such as trifluoromethyl, fluoromethyl, chloromethyl, chloroethyl, fluoroethyl, etc. As the hydroxy lower alkyl group, mention is made of hydroxy alkyl groups whose carbon number ranges from about 1 to about 4, such as hydroxymethyl, hydroxyethyl, hydroxypropyl, hydroxybutyl, etc. As the acyloxy lower alkyl group, mention is made of alkyl groups whose carbon number ranges from about 1 to about 4, which are substituted with, for example, a lower alkanoyloxy group whose carbon number ranges from about 2 to about 5 or benzoyloxy group such as acetoxyethyl, benzoyloxyethyl, etc. As the lower alkoxy lower alkyl group, mention is made of alkyl groups whose carbon number ranges from about 1 to about 4, which are substituted with, for example, an alkoxy group whose carbon number ranges from about 1 to about 4 such as methoxyethyl, ethoxyethyl, propoxyethyl, butoxyethyl, methoxypropyl, ethoxypropyl, ethoxybutyl, etc. As the lower alkoxy group, mention is made of alkoxy groups whose carbon number ranges from about 1 to about 4 such as methoxy, ethoxy, propoxy, isopropoxy, butoxy, isobutoxy, sec-butoxy, tert-butoxy, etc. As the halo lower alkoxy group, mention is made of alkoxy groups whose carbon number ranges from about 1 to about 4, which are substituted with 1 to 3 halo groups such as chloroethoxy, fluoroethoxy, difluoroethoxy, trifluoroethoxy, chloropropoxy, chlorobutoxy, etc. As the lower alkoxy carbonyl lower alkoxy group, mention is made of alkoxy groups whose carbon number ranges from about 1 to about 4, which are substituted with an alkoxycarbonyl group, the carbon number of the alkoxy moiety of which ranges from about 1 to about 4, such as methoxycarbonylmethoxy, ethoxycarbonylmethoxy, butoxycarbonylmethoxy, methoxycarbonylpropoxy, ethoxycarbonylethoxy, etc. Examples of the lower alkenyloxy group include alkenyloxy groups whose carbon number ranges from about 2 to about 5, such as vinyloxy, allyloxy, butenyloxy, etc. As the aralkyloxy group, mention is made of phenyl lower alkyloxy groups, the carbon number of the lower alkyl moiety of which ranges from about 1 to about 4, such as benzyloxy, phenethyloxy, 3-phenylpropyloxy, α-methylphenethyloxy, α-methylbenzyloxy, α-ethylbenzyloxy, β-ethylphenthyloxy, β-methylphenethyloxy, etc. As the lower alkoxy lower alkoxy group, mention is made of alkoxy groups whose carbon number ranges from about 1 to about 4, which are substituted with, for example, an alkoxy group whose carbon number ranges from about 1 to about 4, such as ethoxymethoxy, methoxyethoxy, butoxyethoxy, ethoxypropoxy, etc. Examples of the lower alkoxycarbonyl group include alkoxycarbonyl groups, the carbon number of the alkoxy moiety of which ranges from about 1 to about 4, such as methoxycarbonyl, ethoxycarbonyl, propoxycarbonyl, butoxycarbonyl, etc. As the N,N-di-lower alkylcarbonyl group, mention is made of N,N-dialkylcarbamoyl groups, the carbon number of each alkyl moiety of which ranges from about 1 to about 4, such as N,N-dimethylcarbamoyl, N,N-diethylcarbamoyl, N,N-dipropylcarbamoyl, N,N-dibutylcarbamoyl, N-ethyl-N-methylcarbamoyl, etc., and groups forming 5- or 6-membered ring structure (e.g. N-pyrrolidinylcarbonyl, piperidinocarbonyl) by combining dialkyl moieties together. As the N-lower alkylcarbamoyl group, mention is made of N-alkylcarbamoyl groups, the carbon number of the alkyl moiety of which ranges from about 1 to about 4, such as N-methylcarbamoyl, N-ethylcarbamoyl, N-propylcarbamoyl, N-butylcarbamoyl, etc. As the halo group, mention is made of halogeno groups such as chloro, fluoro, bromo, iodo, etc. As the acyloxy group, mention is made of alkanoyloxy groups, the carbon number of which ranges from about 2 to about 5, such as acetoxy, propanoyloxy, butyryloxy, pivaloyloxy, etc., and benzoyloxy group. As the lower alkylsulfonylamino group, mention is made of alkylsulfonylamino groups, the carbon number of which ranges from about 1 to about 4, such as methanesulfonylamino, ethanesulfonylamino, etc. Examples of the acylamino group include alkanoylamino groups, whose carbon number ranges from about 2 to about 5, such as acetamido, propanoylamino, butyrylamino, pivaloylamino, etc. and benzamido group. As the lower alkoxycarbonylamino group, mention is made of alkoxycarbonylamino groups, the carbon number of the alkoxy moiety of which ranges from about 1 to about 4, such as methoxycarbonylamino, ethoxycarbonylamino, propoxycarbonylamino, butoxycarbonylamino, etc. As the acyl group, mention is made of alkanoyl groups, the carbon number of which ranges from about 2 to about 5, such as acetyl, propanoyl, butyryl, pivaloyl, etc., and benzoyl group. As the lower alkylthio group, mention is made of alkylthio groups, the carbon number of which ranges from about 1 to about 4, such as methylthio, ethylthio, propylthio, butylthio, etc. As the lower alkylsulfinyl group, mention is made of alkylsulfinyl groups, the carbon number of which ranges from about 1 to about 4, such as methylsulfinyl, ethylsulfinyl, propylsulfinyl, butylsulfinyl, etc. As the lower alkylsulfonyl group, mention is made of alkylsulfonyl groups, the carbon number of which ranges from about 1 to about 4, such as methylsulfonyl, ethylsulfonyl, propylsulfonyl, butylsulfonyl, etc.

Specific examples of the substituted phenyl group shown by the above-mentioned A include 3,4-dimethoxyphenyl, 3,4,5-trimethoxyphenyl, 3,4,5-triethoxyphenyl, 3-methoxy-5-nitro4-n-propoxyphenyl, 3,4-dimethoxy-5-methylsulfonylphenyl, 3-chloro-4,5-dimethoxyphenyl, etc. Examples of substituted monocyclic, dicyclic or tricyclic heterocyclic groups include 3-coumarinyl, 6-methoxy-3-coumarinyl, 7-methoxy-3-coumarinyl, 6-methyl-3-coumarinyl, 7-n-butoxycoumarinyl, 6-methoxy-2benzofuranyl, 7-ethoxy-2-benzofuranyl, 1-hydroxy-1,2,3,4-tetrahydrodibenzothiophen-2-yl, 3-oxospiro[benzofuran-2(3H), 1'-cyclopropan]-5yl, 3-hydroxyspiro[benzofuran-2(3H), 1'-cyclopropan]-5-yl, 7,8-dimethoxy-2,3-dihdyro-1-benzoxepin4-yl, 7-methoxy-2,3-dihydro-1-benzoxepin-4-yl, 8-propoxy2,3-dihydro-1-benzoxepin-4-yl, 7-methoxy-8-methyl-2,3- dihydro-1-benzoxepin-4-yl, 7,8-dimethoxy-2,3,4,5-tetrahydro-1-benzoxepin-4-yl, 7-chloro-8-methoxy-2,3-dihydro-1-benzoxepin-4-yl, 7,8-dimethyl- 2,3-dihydro-1-benzoxepin-4-yl, 7,8-dimethoxy-2,3-dihydro-1-benzothiepin-4-yl, 8-methoxy2,3-dihydro-1-benzothiepin-4-yl, 1-oxo-2,3-dihydro-1-benzothiepin-4-yl, 1,1-dioxo-2,3-dihydro-1-benzothiepin-4-yl, 7,8-dimethoxy-1-oxo-2,3-dihydro-1-benzothiepin-4-yl, 7,8-dimethoxy-1,1-dioxo-2,3-dihydro-1-benzothiepin-4-yl, etc.

Preferable examples of A include phenyl group substituted with 2 to 3 lower alkoxy groups (more preferably methoxy group or ethoxy group) or optionally substituted oxygen-containing condensed dicyclic or tricyclic heterocyclic groups (benzo-1,3-dioxolyl, coumarinyl, 2,3-dihydro-1-benzoxepinyl, dibenzofuranyl, 5,6-dihydronaphtho[2,3-d]-1,3-dioxolyl, 6,7-dihydrocyclohepta[f]-1,3-benzodioxolyl, etc.).

Examples of the lower alkyl group shown by $R^1$, $R^2$ or $R^3$ include alkyl groups, the carbon number of which ranges from about 1 to about 4, such as methyl group, ethyl group, propyl group, etc. $R^1$, $R^2$ and $R^3$ may be the same or different from one another, while it is preferable that $R^1$, $R^2$ and $R^3$ are all methyl group. As X, carbonyl group is preferable.

The present invention further provides novel 1,4-disubstituted piperazine compounds and salts thereof, which are useful as a PAF-antagonistic agent.

Among them, compounds of the formula (I'):

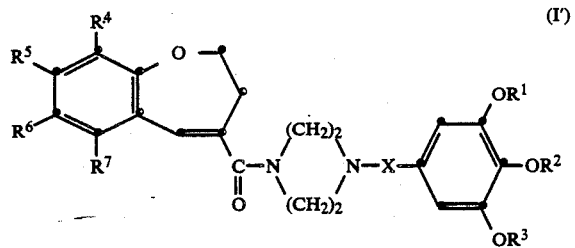

[wherein $R^1$, $R^2$, $R^3$ and X are of the same meaning as defined above; $R^4$, $R^5$, $R^6$ and $R^7$ each stand for hydrogen or a substituent of the phenyl group or heterocyclic group shown by the above-mentioned A] and salts thereof are preferable.

Among the compounds of the formula (I'), those wherein $R^4$ and $R^7$ are hydrogen, and $R^5$ and $R^6$ are a lower alkoxy group (more preferably methoxy group) are further preferable.

Among the compounds of the formula (I) and (I'), those wherein X is methylene group may form salts with an inorganic acid such as hydrogen chloride, hydrogen bromide, sulfuric acid, nitric acid, phosphoric acid, etc. or an organic acid such as acetic acid, tartaric acid, citric acid, fumaric acid, maleic acid, toluenesulfonic acid, methanesulfonic acid, etc., or may form quaternary salts with a lower alkyl halide, the carbon number of the alkyl moiety of which ranges from about 1 to about 4, (e.g. methyl iodide, ethyl iodide, propyl iodide). As the salts of the compounds (I), pharmaceutically acceptable ones are preferable, and pharmaceutically acceptable acid addition salts are more preferable. Hydrates of the compounds (I) are also usable.

The compound (I) of the present invention can be prepared by, for example, subjecting a compound represented by the formula: A-COOH (II) [wherein A is of the same meaning as defined above] and a compound represented by the formula:

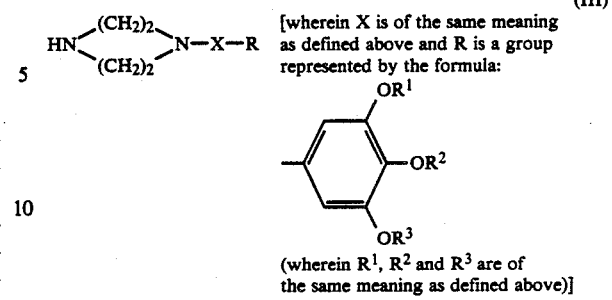

[wherein X is of the same meaning as defined above and R is a group represented by the formula:

(wherein $R^1$, $R^2$ and $R^3$ are of the same meaning as defined above)]

to dehydrative condensation.

The dehydrative condensation can be conducted by, for example, a conventional reaction for forming an amido-bond. More concretely stating, the dehydrative condensation is carried out by using singly an amide-forming reagent such as dicyclohexylcarbodiimide, N,N'-carbonyldiimidazole, diphenyl phosphoryl azide, diethyl phosphorocyanidate, etc.; or by allowing a compound (II) to react with a compound (III), after converting the compound (II) to an active ester by subjecting a phenol such as 2,4,5-trichlorophenol, pentachlorophenol, pentafluorophenol, 2-nitrophenol or 4-nitrophenol, etc., or an N-hydroxy compound such as N-hydroxysuccinimide, 1-hydroxybenztriazole, N-hydroxypiperidine, N-hydroxy-5-norbornene-2,3-dicarboxyimide, etc. to condensation in the presence of a catalyst such as dicyclohexylcarbodiimide, etc.; or by allowing a compound (II) to react with a compound (III), after converting the compound (II) to a mixed acid anhydride by allowing it to react with an acid chloride such as ethyl chlorocarbonate, isobutyl chlorocarbonate, benzyl chlorocarbonate, etc. This amide-bond-forming reaction can be accelerated, either by allowing a compound (II) to react directly with a compound (III) or by allowing a compound (II) to react with a compound (III) after converting the former to its active ester or mixed acid anhydride, by the addition of preferably an organic base such as tertiary amines (e.g. triethylamine, N-methylpiperidine). The reaction temperature ranges usually from about $-20°$ C. to about $+50°$ C., preferably from about $-10°$ C. to about $+25°$ C. Examples of the solvent usually employed include dioxane, tetrahydrofuran, acetonitrile, pyridine, N,N-dimethylformamide, N,N-dimethylacetamide, dimethylsulfoxide, N-methylpyrrolidone, chloroform, methylene chloride, etc., and these may be used singly or as a suitable mixture.

The compound (I) of the present invention can also be prepared by, for example, allowing a compound represented by the formula: A-COW (IV) [wherein A is of the same meaning as defined above; W stands for a halogen atom] to react with a compound (III). This reaction can be allowed to proceed usually in the presence or absence of water or any other organic solvent (acetonitrile, dimethylformamide, dimethylacetamide, dimethylsulfoxide, tetrahydrofuran, benzene, toluene, ethyl acetate, chloroform, methylene chloride), by keeping the temperature range from about $-20°$ C. to about $+150°$ C. In this case, for the purpose of accelerating the reaction rate, a base such as potassium carbonate, sodium hydroxide, sodium hydrogencarbonate, pyridine, triethylamine, etc. can be allowed to coexist in the reaction system.

The compound (I) of the present invention can also be prepared by allowing a compound represented by the formula:

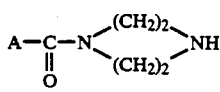

[wherein A is of the same meaning as defined above] to react with a compound represented by the formula: Y-X-R (VI) [wherein R and X are of the same meaning as defined above; Y stands for halogen (X: methylene group or carbonyl group) or a group represented by the formula $R^aSO_2$—O— (wherein $R^a$ stands for a lower ($C_{1-4}$) alkyl, trifluoromethyl, phenyl or p-tolyl) (X: methylene group or )]. The reaction can be allowed to proceed in water or any other organic solvent (e.g. acetonitrile, dimethylformamide, dimethylacetamide, dimethylsulfoxide, tetrahydrofuran, acetone, methyl ethyl ketone, benzene, toluene) singly or in an admixture thereof, while keeping the temperature ranging from about −20° C. to about +150° C. In this case, a base such as potassium carbonate, sodium hydroxide, potassium hydroxide, pyridine, triethylamine, etc. can be allowed to coexist in the reaction system.

The compound (I) of the present invention, wherein X is carbonyl group, is prepared by, for example, subjecting a compound (V) and a compound represented by the formula: HOOC-R (VII) [wherein R is of the same meaning as defined above] to dehydrative condensation. This dehydrative condensation reaction can be conducted in a manner similar to that of the compound (II) with the compound (III).

And, the compound (I) of the present invention, wherein X is methylene group, can also be prepared by, for example, subjecting a compound (V) and compound represented by the formula:

 [wherein R is of the same meaning as defined above] (VIII)

to condensation under reductive conditions.

As the reductive conditions, mention is made of, for example, catalytic reduction using as the catalyst a metal such as platinum, palladium, Raney nickel, rhodium, etc. or a mixture of the metal and an optional carrier (e.g. carbon); reduction by means of a metallic hydride such as lithium aluminium hydride, lithium borohydride, lithium cyanoborohydride, sodium borohydride, sodium cyanoborohydride, etc.; reduction by means of metallic sodium, metallic magnesium, etc. and alcohols; reduction by means of a metal such as iron, zinc, etc. and an acid such as hydrochloric acid, acetic acid, etc.; electrolytic reduction; reduction by means of reductase; etc. The above-mentioned reaction is usually carried out in the presence of water or an organic solvent (e.g. methanol, ethanol, ethyl ether, dioxane, methyelne chloride, chloroform, benzene, toluene, acetic acid, N,N-dimethylformamide, N,N-dimethylacetamide), and the reaction temperature varies with the reduction process then employed, but, in general, preferably ranges from about −20° C. to about +100° C. This reaction can attain the purpose satisfactorily by carrying out under normal pressure, but it may be conducted, depending on convenience, under elevated or reduced pressure.

The intended compound (I) of the present invention thus obtained can be isolated from the reaction mixture by a conventional separating and purifying means (e.g. extraction, concentration, neutralization, filtration, recrystallization, column chromatography, thin-layer chromatography).

Salts of the compound (I) can be obtained, in some instances, by the reaction per se for preparing the compound (I), but, upon necessity, they can be prepared by the addition of an acid or an alkyl halide.

The starting compounds (III), (V) and (VI) can be synthesized by, for example, the following processes.

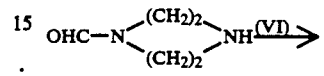

(IX)

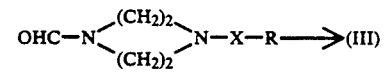

(XI)

The reaction between the above compounds (IX) and (VI) can be conducted similarly to that between the compounds (V) and (VI). The reaction of the above compounds (XI)→(III) is deformylation, and it is carried out in water or an organic solvent (e.g. methanol, ethanol, dioxane, tetrahydrofuran, acetonitrile, acetone, dimethylsulfoxide) or a mixture thereof at 0° C.~+100° C. in the presence of an acid (e.g. hydrogen chloride, hydrogen bromide, sulfuric acid) or a base (e.g. potassium hydroxide, sodium hydroxide).

A compound (III) wherein X is a thiocarbonyl group can be obtained by allowing a compound (III) wherein X is a carbonyl group to react with a Lawesson reagent.

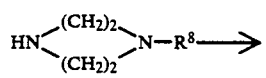

(XII)

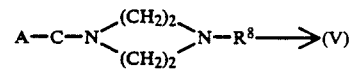

(XIII)

[wherein $R^8$ stands for formyl group or benzyl group]

The reaction between the above-mentioned compounds (XII) and (IV) can be conducted in a manner similar to that between the compounds (III) and (IV). The reaction of (XIII)→(V) is deformylation or debenzylation, and the deformylation can be conducted in a manner similar to that of the reaction of (XI)→(III). The debenzylation can be conducted by catalytic reduction, and the catalytic reduction is conducted in water or an organic solvent (e.g. methanol, ethanol, ethyl acetate, dioxane, tetrahydrofuran) or a mixture thereof in the presence of a suitable catalyst such as palladium-carbon. This reaction is conducted under normal pressure to about 150 kg/cm at temperatures ranging from 0°·C. to +150° C., and, for accelerating the reaction rate, an acid (e.g. hydrogen chloride, hydrogen bromide, hydrogen fluoride, sulfuric acid) may be added to the reaction system.

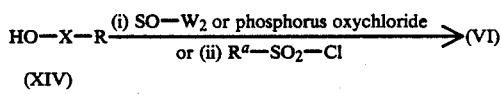

[wherein W is of the same meaning as defined above]

The above reaction (i) is conducted in a suitable organic solvent (e.g. benzene, toluene, ether) at temperatures ranging from about 0° C. to about 120° C. in the presence or absence of a base (e.g. pyridine, dimethylaniline, triethylamine) (X=carbonyl group or methylene group). The above reaction (ii) is conducted in a suitable organic solvent (e.g. benzene, toluene, ether) at temperatures ranging from about −20°C to about +25° C. in the presence of a base (e.g. pyridine) (X=methylene group). Incidentally, the reaction can be conducted using a base as the solvent.

And, the compound (IV) can be obtained by subjecting the compound (II) as the starting compound to a reaction similar to that of the reaction of (XIV)→(VI) (i).

The compound (II) can easily be synthesized by a method described in literature references [e.g. Jacques et al., Bull. Soc. Chim. Fr., 512(1950); Hashem et al.,J. Med. Chem., 19, 229(1976); Itoh et al., Chem. Pharm. Bull., 26, 504 (1978); Miyake et al., Chem. Pharm. Bull., 31, 2329(1983); Itoh et al., Chem. Pharm. Bull., 32, 130(1984); Tamura et al., J. Agr. Chem. Soc. Japan 27, 318(1953); Organic Syntheses, 26, 28(1946)] or methods analogous thereto. For example, when the compound (II) is a compound represented by the formula:

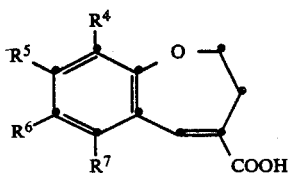

[each symbol is of the same meaning as defined above], it can be easily synthesized in accordance with the following reaction schema.

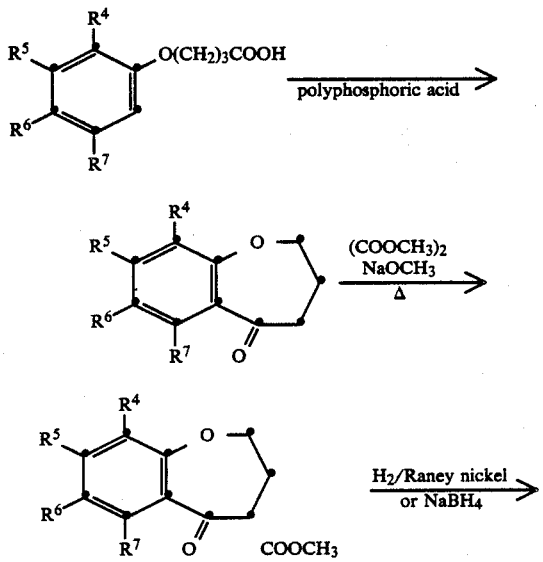

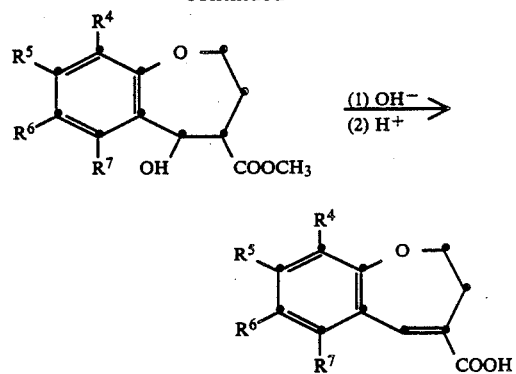

The compound (I) and salts thereof exhibit excellent PAF antagonism and are useful as prophylactic and therapeutic agents of circulatory disturbances due to PAF, for example, thrombosis, apoplexy (e.g. cerebral hemorrahge, cerebral thrombosis), myocardial infarction, angina pectoris, venous thrombosis, nephritis (e.g. gluomerulonephritis), diabetic nephritides, shock (e.g. endotoxin shock observed after grave infectious diseases or postoperative shock, intravascular hemagglutination syndrome caused by endotoxin, anaphylactic shock, hemorrhagic shock); gastroenteric diseases caused by PAF (e.g. gastric ulcer); diseases associated with allergy and inflammation (e.g. bronchial asthma, psoriasis); pneumonia; rejection symptoms associated with increase in the amount of PAF produced in the case of internal organ transplantation; insufficiency of internal organs (e.g. heart, liver, kidney) in the case of internal organ operation. The compound (I) and salts thereof are low in toxicity, and can therefore be administered orally or non-orally as they are in a form of powder or as a pharmaceutical composition in a suitable dosage form, to mammals (e.g. man, rabbit, dog, cat, rat, mouse). The dosage varies depending upon the subject to be administered, disease to be treated, conditions thereof and route of administration, and when the compound (I) or a salt thereof is used for prophylaxis or therapy of shock in a human adult, it is convenient to administer through intravenous injection usually in a single dose in the range of from about 0.01 to about 20 mg/kg body weight, preferably in the range of from about 0.1 to about 10 mg/kg body weight, more preferably in the range of from about 0.1 to about 2 mg/kg body weight, about once to five times a day, preferably about once to three times a day. And, the compound (I) or a salt thereof can be administered through drip injecition in a single dose in the range of from about 0.01 to about 1.0 mg/kg body weight/min. for about one hour, about once to five times a day, preferably once to three times a day. The dosages for other non-oral routes as well as the oral dosage may be selected referring to the above-mentioned dose levels. When shock symptoms are very serious, dosage may be increased depending on the symptoms.

When the compound (I) or a salt thereof is used orally for the prophylaxis or therapy of, for example, thrombosis, bronchial asthma, nephritis, etc. in a human adult, it is convenient to administer usually in a single dose in the range of from about 0.05 to about 20 mg/kg body weight, preferably in the range of from about 0.2 to about 5 mg/kg body weight, about once to five times, preferably from once to three times. The dosages for other non-oral routes may be selected referring to the above-mentioned dose levels.

The pharmaceutical composition to be used for the above administration comprises an effective amount of the compound (I) or a salt thereof and a pharmaceutically acceptable carrier or excipient, and the said composition is provided in a dosage form suitable for oral or non-oral administration.

The composition for oral administration includes, for example, solid or liquid dosage forms, and as their examples, there may be mentioned tablets (inclusive of sugar-coated tablets and film-coating tablets), pills, granules, powders, capsules (inclusive of soft capsules), syrups, emulsions, suspensions, etc. Such compositions can be manufactured by per se known procedures and comprise carriers and excipients commonly used in the pharmaceutical industry. Examples of the carriers and excipients for the preparation of tablets include lactose, starch, sugar, magnesium stearate, etc.

The compositions for non-oral administration include, for example, injections, suppositories, ointments, fomentations, paints, etc., and as examples of injectables, there may be mentioned dosage forms, such as injectable solutions for intravenous injection, for subcutaneous injection, for intracutaneous injection, for intramuscular injection, for drip injection, etc. Such injectable solutions are prepared by per se known procedures, for example, by dissolving, suspending or emulsifying the compound (I) or a salt thereof in a sterile aqueous or oily solution usually employed for injectable solutions. The aqueous solution for injection includes, for example, physiological saline solution, isotonic solution containing glucose and other adjuvants, and may be employed in combination with a suitable solubilizer, such as alcohols (e.g. ethanol), polyalcohols (e.g. propylene glycol, polyethylene glycol), and nonionic surface active agents [e.g. polysorbate 80, HCO-50 (polyoxyethylene (50 mol.) adduct of hydrogenated castor oil)], etc. The oily solution includes, for example, sesame oil, soybean oil, etc., and may be used in combination with a solubilizer e.g. benzyl benzoate, benzyl alcohol, etc. The injectable solution preapred is usually filled into suitable ampoules to be supplied as injectable preparations. The suppositories for rectal administration are preapred by a per se known procedure, for example, by incorporating the compound (I) or a salt thereof into a conventional base material for suppository use, followed by moulding.

The above-mentioned compositions may contain any other active components, so long as they do not cause undesirable interactions by the incorporation with the compound (I) or a salt thereof. For example, to mammals suffering from infectious diseases, an antibiotic may be administered together with the compound (I) or a salt thereof for preventing endotoxin-shock.

(WORKING EXAMPLES)

The working examples herein represent specific embodiments of the present invention but are not to be construed as limiting the scope thereof.

REFERENCE EXAMPLE 1

A mixture of 5-nitrovanillin (10 g), propyl iodide (25 g), potassium carbonate (10 g) and N,N-dimethylformamide (200 ml) is stirred at 100° C. for 24 hours. After cooling, water (500 ml) is added to the reaction mixture, followed by extraction with ethyl acetate (200 ml). The extract solution is washed with water, dried and, then, distilled off under reduced pressure. The residue is purified by means of a silica gel column chromatography (hexane: ethyl acetate=2:1-1:1) to afford 4-propoxy-3-methoxy-5-nitrobenzaldehye (6 g) as a pale yellow oily product. This product is dissolved in acetone (200 ml), and potassium permanganate (18 g) is added to the solution. The mixture is stirred at room temperature overnight. To the reaction mixture are added ethanol (50 ml), water (50 ml) and acetone (200 ml). The whole mixture is stirred for two hours, and filtered off. The filtrate is concentrated under reduced pressure. Precipitating crystals are collected by filtration to give 3-methoxy-5-nitro-4-propoxy benzoic acid (2.2 g) as colorless crystals. This product is recrystallized from a mixture of ethanol and water to give colorless needles, m.p. 121°–123° C.

Elemental Analysis for $C_{11}H_{13}NO_6$:
Calcd.: C 51.77; H 5.13; N 5.49;
Found: C 51.74; H 5.20; N 5.48.

REFERENCE EXAMPLE 2

A mixture of 5-nitrovanillin (2.2 g), butyl chloride (10 ml), potassium carbonate (8 g) and N,N-dimethylformamide (50 ml) is stirred at 100° C. for 24 hours. After cooling, water (300 ml) is added to the reaction mixture, followed by extraction with ethyl acetate (200 ml). The extract solution is washed with water, dried, and concentrated under reduced pressure. The residue is purified by means of a silica gel column chromatography (hexane: ethyl acetate=1:1) to afford 4-butoxy-3-methoxy-5-nitrobenzaldehye (2 g) as a pale yellow oily product. This product is dissolved in acetone (100 ml), potassium permanganate (6 g) is added to the mixture, and the mixture is stirred at room temperature overnight. To the reaction mixture are added ethanol (20 ml), water (20 ml) and acetone (200 ml). The whole mixture is left standing for two hours, then insolubles are filtered off. The filtrate is concentrated under reduced pressure. The concentrate is dissolved in water (100 ml) and the mixture is acidified with concentrated hydrochloric acid. Precipitating crystals are collected by filtration to afford 4-butoxy-3-methoxy-5-nitrobenzoic acid (1.6 g) as colorless crystals. This product is recrystallized from a mixture of ethanol and water to give colorless prisms, m.p. 114°–115° C.

Elemental Analysis for $C_{12}H_{15}NO_6$:
Calcd.: C 53.53; H 5.62; N 5.20;
Found: C 53.47; H 5.65; N 5.23.

REFERENCE EXAMPLE 3

A mixture of 6,7-methylenedioxy-3,4-dihydro-1(2H)-naphthalenone (3.8 g), diethyl carbonate (36 g) and sodium methylate powder [prepared by subjecting a 28% methanol solution (14 g) of sodium methylate to drying under reduced pressure] is heated under reflux for 3 hours in a nitrogen stream. After cooling, methanol (20 ml) is added to the reaction mixture. The mixture is acidified with concentrated hydrochloric acid, and mixed with water (200 ml) and ethyl acetate (200 ml), followed by extraction. The organic layer is washed with water, dried and concentrated under reduced pressure to leave methyl 6,7-methylenedioxyl-oxo-1,2,3,4-tetrahydro-2-naphthoate as oily product. This product is dissolved in methanol (50 ml). Sodium borohydride (0.5 g) is added to the mixture under ice-cooling, and the mixture is stirred. Thirty minutes later, sodium borohydride (0.5 g) is supplemented, and the mixture is stirred for 30 minutes, followed by subjecting it to extraction with the addition of water and ethyl acetate. The organic layer is washed with water, dried, concentrated to dryness under reduced pressure. To the residue is added ethyl acetate (10 ml), and the mixture is left standing to allow crystals to precipitate. The crystals are collected by filtration to afford methyl 1-hydroxy-6,7-methylenedioxy-1,2,3,4-tetrahydro-2-naphthoate (1 g) as colorless prisms. The filtrate is concentrated to dryness under reduced pressure. The residue is purified by means of a silica gel column chromatography (hexane: ethyl acetate=2:1–1:1) to thereby obtain the same product (1 g). The overall yield is 2 g. Melting point=120°–130°C.

Elemental Analysis for $C_{13}H_{14}O_5$:
Calcd.: C 62.39; H 5.64;
Found: C 62.47; H 5.70.

This product (2 g) is dissolved in methanol (30 ml). A 1N aqueous solution of sodium hydroxide (20 ml) is added dropwise to the solution at 60° C. The mixture is stirred for 30 minutes. After addition of water (100 ml), the mixture is extracted with ethyl ether (30 ml). The aqueous layer is acidified with concentrated hydrochloric acid, followed by extraction with ethyl acetate (200 ml). The extract solution is concentrated to dryness under reduced pressure. To the residue is added dioxane (20 ml), concentrated hydrochloric acid (2 ml) and water (10 ml), then the mixture is left standing at room temperature for 30 minutes. The reaction mixture is concentrated under reduced pressure to allow crystals to precipitate. To the crystals is added water, then the crystals are collected by filtration, followed by recrystallization from a mixture of acetone and water to afford 6,7-methylenedioxy-1,2-dihydro3-naphthoic acid as colorless prisms (1.1 g), m.p. 250°–252° C. (decomp.)

Elemental Analysis for $C_{12}H_{10}O_4$: :
Calcd.: C 66.05; H 4.62;
Found: C 66.26; H 4.66.

REFERENCE EXAMPLE 4

A 28% methanol solution (14 g) of sodium methoxide is concentrated to dryness under reduced pressure, and the residue is pulverized. To the powder are added dimethyl carbonate (36 g) and 7-methoxy-3,4-dihydro-2H-dibenzofuran-1-one (4.3 g) [Bhide et al. Tetrahedron, 10, 223 (1960)]. The mixture is heated under reflux for two hours in a nitrogen stream. After cooling, water (200 ml) and ethyl acetate (200 ml) are added to the reaction mixture. To the mixture is added dropwise, while stirring, concentrated hydrochloric acid to thereby acidify the system, followed by stirring for 30 minutes. Then precipitating crystals are collected by filtration to give methyl 7-methoxy-1-oxo1,2,3,4-tetrahydrodibenzofuran-2-carboxylate as pale yellow crystals (3.1 g). The ethyl acetate portion of the mother liquor is separated, washed with water and dried, followed by concentration under reduced pressure to make the volume to be about 50 ml to thereby cause precipitation of pale yellow crystals (1 g). The overall yield is 4.1 g. Melting point: 173°–175° C.

Elemental Analysis for $C_{15}H_{14}O_5$:
Calcd.: C 65.69; H 5.14;
Found: C 65.95; H 5.15.

This product (4.1 g) is dissolved in a mixture of methylene chloride (100 ml) and methanol (100 ml). Sodium borohydride (0.25 g) is added in small portions to the solution with stirring at room temperature. After stirring for 30 minutes, sodium borohydride (0.25 g) is supplemented to the mixture. The mixture is stirred for 40 minutes. Water (300 ml) and methylene chloride (200 ml) are added to the reaction mixture, mixed, and the organic layer is separated. The organic layer is washed with water, and dried, followed by distilling off the solvent under reduced pressure to leave an oily product. To the product are added ethyl ether (30 ml) and hexane (20 ml), and the mixture is left standing to cause precipitation of methyl 1-hydroxy-7-methoxy-1,2,3,4-tetrahydrodibenzofuran-2-carboxylate as pale yellow crystals (2.0 g). This product is recrystallized from ethyl ether to give colorless prisms,
m.p. 130°–135° C.

Elemental Analysis for $C_{15}H_{18}O_5$
Calcd.: C 65.21; H 5.84;
Found: C 65.45; H 5.84.

In methanol (100 ml) is dissolved the hydroxy compound (2 g) obtained above. To the solution is added dropwise, while stirring at room temperature, a 1N aqueous solution of sodium hydroxide (100 ml). After addition of water (100 ml), the mixture is left standing for 30 minutes to cause precipitation of crystals. The crystals are collected by filtration. Further, the mother liquor is concentrated under reduced pressure (about 50 ml), then precipitating crystals are collected by filtration. These crystals are combined and washed with ethyl acetate, then dissolved in a mixture of acetone (200 ml) and concentrated hydrochloric acid (5 ml). The solution is left standing at room temperature for one hour. The reaction mixture is concentrated under reduced pressure. Water (50 ml) is added to the residue. Precipitating crystals are collected by filtration to yield 7-methoxy-3,4-dihydrodibenzofuran-2-carboxylic acid (1.5 g) as yellow needles, m.p. 228°–231° C.

Elemental Analysis for $C_{14}H_{12}O_2$:
Calcd.: C 68.85; H 4.95;
Found: C 69.25; H 4.97.

A 28% sodium methylate - methanol solution (14 g) is concentrated dryness under reduced pressure. The residue is then pulverized. To the powdery compound are added dimethyl carbonate (36 g) and 3,4-dihydro-1(2H)-dibenzothiophen-1-one (4.04 g) [Mitra et al., Chem. Abstr. 51, 5784 (1957)], and the mixture is heated for two hours under reflux in a nitrogen stream. After addition of water (100 ml) and petroleum ether (100 ml), the reaction mixture is acidified with concentrated hydrochloric acid. Then precipitating crystals are collected by filtration to give methyl 1-oxo-1,2,3,4- tetrahydro-2-dibenzothiophenecarboxylate (4.5 g). This product is recrystallized from a mixture of methanol and acetone to give colorless needles, m.p. 158°–160° C.

Elemental Analysis for $C_{14}H_{12}O_3S$:
Calcd.: C 64.60; H 4.65;
Found: C 64.37; H 4.64.

This product (4.5 g) is dissolved in a mixture of methylene chloride (100 ml) and methanol (100 ml). To the solution is added sodium borohydride (0.5 g), and the mixture is stirred for 45 minutes. To the reaction mixture is added water (500 ml), and the methylene chloride layer is separated. The remaining aqueous layer is subjected to extraction with methylene chloride. The methylene chloride layer is combined, washed with water, dried and concentrated to dryness under reduced pressure. The residue is dissolved in methanol (30 ml). A 1N aqueous solution of sodium hydroxide (50 ml) is added dropwise to the solution above obtained at room temperature. The mixture is stirred for 30 minutes, and diluted with ethyl acetate (50 ml). The whole mixture is left standing. The precipitating crystals are collected by filtration. The mother liquor is concentrated under reduced pressure and water (50 ml) is added to the residue. Then precipitating crystals are collected by filtration. These crystal portions are combined, washed with ethyl acetate, followed by adding to a mixture of dioxane (30 ml), concentrated hydrochloric acid (4 ml) and water (30 ml). The whole mixture is left standing for one hour at room temperature, and then concentrated under reduced pressure. Resultant crystalline precipitates are collected by filtration to yield 1-hydroxy-1,2,3,4-tetrahydro-2-dibenzothiophene carboxylic acid (2 g). This product is recrystallized from a mixture of methanol and water to give colorless needles, m.p. 152°–154° C. (decomp.).

Elemental Analysis for $C_{13}H_{12}O_3S$:
Calcd.: C 62.88; H 4.87;
Found: C 62.74; H 4.74.

REFERENCE EXAMPLE 6

In a mixture of acetone (50 ml) and concentrated hydrochloric acid (5 ml) is dissolved 1-hydroxy-1,2,3,4-tetrahydro-2-dibenzothiophene carboxylic acid (1.2 g). The solution is stirred at 80° C. for two hours. The reaction mixture is cooled, then precipitating crystals are collected by filtration to give 3,4-dihydro-2-benzothiophene carboxylic acid (0.8 g) as pale yellow needles.

Melting point:
Gradually decomposed, but no definite decomposition point is observed.

Elemental Analysis for $C_{13}H_{10}O_2S$:
Calcd.: C 67.80; H 4.38;
Found: C 67.83; H 4.37.

REFERENCE EXAMPLE 7

In ethanol (50 ml) is dissolved 3,4-dimethoxythiophenol (28 g), to the resulting mixture is added an ethanol solution (77 ml) of 2.5M sodium hydroxide, and the mixture is heated for 10 minutes under reflux. To the reaction mixture is then added τ-butyrolactone (18.5 g) and the mixture is heated for 3 hours under reflux. To the reaction mixture is added water (100 ml), then ethanol is distilled off under reduced pressure. The remaining aqueous solution is washed with ethyl acetate, and the aqueous layer is acidified with dilute hydrochloric acid. The mixture is extracted with ethyl acetate. The organic layer is washed with water and dried, followed by distilling off the solvent under reduced pressure. The residue is recrystallized from ether-hexane to afford 4-(3,4-dimethoxyphenylthio)butyric acid as colorless prisms (m.p. 78° C.) (20.5 g). Then, 4-(3,4dimethoxyphenylthio)butyric acid (14.5 g) is added to polyphosphoric acid (183 g), and the mixture is stirred at 100° C. for two hours. The reaction mixture is poured into ice-water (500 ml), followed by extraction with ethyl acetate. The organic layer is washed with water, dried, and concentrated under reduced pressure. The residue is purified by means of a silica gel column chromatography (eluent:hexane - ethyl acetate=5:1) to afford 7,8-dimethoxy-3,4-dihydro-1-benzothiepin-5(2H)-one (12.0 g). Recrystallization of the product from hexane - methylene chloride give colorless prisms, m.p. 128°–129° C.

Elemental Analysis for $C_{12}H_{14}O_3S$:
Calcd.: C 60.48; H 5.92;
Found: C 60.62; H 6.00.

REFERENCE EXAMPLE 8

To dimethyl carbonate (87 g) is added sodium methoxide (10.5 g), to the mixture is added 7,8-dimethoxy-3,4-dihydro-1-benzothiepin-5(2H)-one(11.0 g) obtained in Reference Example 7. The mixture is heated for two hours under reflux. The reaction mixture is poured into ice-water and acidified (pH 3) with 2N hydrochloric acid, followed by extraction with ethyl acetate. The organic layer is washed with a saturated aqueous saline solution, dried, and concentrated under reduced pressure. The residue is recrystallized from hexane - methylene chloride to afford methyl 7,8-dimethoxy5-oxo-2,3,4,5-tetrahydro-1-benzothiepin-4-carboxylate as colorless needles (10.8 g), m.p. 132°–133° C.

Elemental Analysis for $C_{14}H_{16}O_5S$:
Calcd.: C 56.74; H 5.44;
Found: C 56.51; H 5.46.

REFERENCE EXAMPLE 9

In a mixture solvent of methanol (50 ml) and methylene chloride (50 ml) is dissolved methyl 7,8-dimethoxy-5-oxo-2,3,4,5-tetrahydro-1-benzothiepin-4-carboxylate (11.4 g) obtained in Reference Example 8. To the solution is added sodium borohydride (2.1 g) in limited amounts taking 6 hours with stirring. Excess sodium borohydride is decomposed with dilute hydrochloric acid, followed by extraction with methylene chloride. The organic layer is washed with a small volume of saturated aqueous saline, dried, and concentrated under reduced pressure. The residue is dissolved in methanol (50 ml), to the solution is added a 7.5 N aqueous solution of sodium hydroxide (10 ml), and the mixture is stirred at room temperature for 1.5 hour. To the reaction mixture is added water. The mixture is acidified (pH 3) with dilute hydrochloric acid, followed by extraction with methylene chloride. The organic layer is concentrated under reduced pressure, and the concentrate is dissolved in dioxane (35 ml). To the solution is added 10N hydrochloric acid (7 ml), and the mixture is stirred at 50° C. for 30 minutes. The reaction mixture is cooled and diluted with water. Then precipitating crude crystals are collected by filtration, washed with water and dried, followed by recrystallization from methylene chloride-ether to give 7,8-dimethoxy-2,3-dihydro-1-benzothiepin-4-carboxylic acid as colorless prisms (6.5 g), m.p. 190°–193° C.

Elemental Analysis for $C_{13}H_{14}O_4S$:
Calcd.: C 58.63; H 5.30;
Found: C 58.55; H 5.37.

REFERENCE EXAMPLE 10

A mixture of 3,4-dimethoxyphenol (10 g), ethyl 4-bromo-butyrate (15.2 g), anhydrous potassium carbonate (11.7 g), potassium iodide (1.5 g) and N,N-dimethylformamide (40 ml) is stirred for 15 hours at 60° to 70° C. The reaction mixture is poured into ice-water and extracted with ethyl acetate. The organic layer is washed with water, dried, and concentrated under reduced pressure. The residue is dissolved in methanol (30 ml), to the solution is added a 2.5N aqueous solution of sodium hydroxide (67 ml), and the mixture is stirred for 40 mintues at 50° to 60° C. The reaction mixture is concentrated under reduced pressure. To the concentrate is added water, and the mixture is acidified (pH 3) with dilute hydrochloric acid, followed by extraction with ethyl acetate. The organic layer is washed with water, dried, and concentrated under reduced pressure. The residue is recrystallized from ethyl acetate - hexane to give 4-(3,4-dimethoxyphenyloxy)butyric acid as colorless prisms (12.5 g). To polyphosphoric acid (60 g) is added 4-(3,4-dimethoxyphenyloxy)butyric acid (6.0 g) obtained above, and the mixture is stirred for 30 minutes at 100° C. The reaction mixture is poured into ice-water and extracted with ethyl acetate. The organic layer is washed with water, dried, and concentrated. The residue is recrystallized from ethyl acetate - hexane to give 7,8-dimethoxy-3,4-dihydro-1benzoxepin-5(2H)-one as colorless prisms, m.p. 87°-88° C.

Elemental Analysis for $C_{12}H_{14}O_4$:
Calcd.: C 64.85; H 6.35;
Found: C 64.85; H 6.38.

REFERENCE EXAMPLE 11

In dimethyl carbonate (70 ml) is dissolved 7,8-dimethoxy-3,4-dihydro-1-benzoxepin-5(2H)-one (4.55 g) obtained in Reference Example 10. Sodium methoxide (7 g) is added to the solution, and heated under reflux for 6 hours in a nitrogen stream. The reaction mixture is cooled and acidified with dilute hydrochloric acid, and extracted with ethyl acetate. The organic layer is washed with water, dried, and concentrated under reduced pressure. The residue is purified by means of a silica gel column chromatography (eluent:hexane -methylene chloride - ethyl acetate=2:1:1) to give methyl 7,8-dimethoxy-5-oxo-2,3,4,5-tetrahydro-1-benzoxepin-4-carboxylate as colorless needles (recrystallized from ethyl acetate - hexane) (4.5 g), m p. 120°-121° C.

Elemental Analysis for $C_{14}H_{16}O_6$:
Calcd.: C 60.00; H 5.75;
Found: C 59.91; H 5.71.

REFERENCE EXAMPLE 12

In a mixture of methylene chloride (60 ml) and methanol (80 ml) is dissolved methyl 7,8-dimethoxy-5-oxo-2,3,4,5-terahydro-1-benzoxepin-4-carboxylate obtained in Reference Example 11 (1.9 g). To the solution is added, while stirring, sodium borohydride (0.6 g) in limited amounts taking one hour. The reaction mixture is treated with dilute hydrochloric acid, followed by extraction with methylene chloride. The organic layer is washed with a small volume of a saturated aqueous saline solution, dried, and concentrated under reduced pressure. The residue is dissolved in methanol (5 ml), and to the solution is added a 2N aqueous solution of sodium hydroxide ( 20 ml). The mixture is stirred at room temperature for two hours. After addition of water (50 ml), the reaction mixture is washed with ether. The aqueous layer is acidified with dilute hydrochloric acid, and extracted with methylene chloride. The organic layer is washed with water, dried, and concentrated under reduced pressure. The residue is dissolved in dioxane (10 ml), to the solution is added concentrated hydrochloric acid (3 ml), and then the mixture is stirred for one hour at 90° C. After cooling, the reaction mixture is extracted with ethyl acetate. The organic layer is washed with water, dried, and concentrated under reduced pressure. The residue is recrystallized from ethyl acetate to afford 7,8-dimethoxy-2,3-dihydro-1-benzoxepin-4carboxylic acid as colorless needles (1.2 g), m. p. 209°-210° C.

Elemental Analysis for $C_{13}H_{14}O_5$:
Calcd.: C 62.39; H 5.64;
Found: C 62.15; H 5.48.

REFERENCE EXAMPLE 13

A mixture of 7-methoxy-3,4-dihydro-1-benzoxepin-5(2H)-one (1.9 g), sodium methoxide (2.8 g) and dimethyl carbonate (40 ml) is heated under reflux for 8 hours with stirring. The reaction mixture is treated in a manner as that in Reference Example 11 to give methyl 7-methoxy-5-oxo2,3,4,5-tetrahydro-1-benzoxepin-4-carboxylate as a colorless oily product (1.7 g). This product (1.6 g) is dissolved in a mixture of methylene chloride (20 ml) and methanol (20 ml). To the solution is added sodium borohydride (0.15 g) in limited amounts. The mixture is stirred. After addition of water, the reaction mixture is extracted with methylene chloride. The organic layers are combined, washed with water, and evaporated to dryness. To the residue are added methanol (5 ml) and 1N aqueous solution of sodium hydroxide (8 ml). The mixture is stirred at 60° C. for 30 minutes. To the reaction mixture are added water and ether, and the mixture is shaken, followed by separating the aqueous layer. The aqueous layer is acidified with dilute hydrochloric acid, and extracted with methylene chloride. The organic layers are combined, washed with water, dried, and concentrated under reduced pressure. To the residue are added dioxane (5 ml) and concentrated hydrochloric acid (1.5 ml), and the mixture is stirred at 100° C. for 30 minutes. After addition of water, the reaction mixture is extracted with ethyl acetate. The organic layer is washed with water, dried, and concentrated under reduced pressure. The residue is recrystallized from ethyl acetate to afford 7-methoxy2,3-dihydro-1-benzoxepin-4-carboxylic acid as colorless scales (0.41 g), m.p. 176°-177° C.

Elemental Analysis for $C_{12}H_{12}O_4$:
Calcd.: C 65.45; H 5.49;
Found: C 65.17; H 5.48.

REFERENCE EXAMPLE 14

A mixture of 8-methoxy-3,4-dihydro-1-benzoxepin-5(2H)-one (3.0 g), sodium methoxide (5 g) and dimethyl carbonate (60 ml) is heated under reflux for 8 hours with stirring in a nitrogen stream. The reaction mixture is treated in a manner as in Reference Example 8 to give 8-methoxy-5-oxo-3,4,5,6-tetrahydro-1-benzoxepin-4-carboxylate as a colorless oily product (3.1 g). This product is dissolved in a mixture of methylene chloride (50 ml) and methanol (70 ml). To the solution is added sodium borohydride (1.0 g) in limited amounts with stirring at room temperature over a period of two hours. After addition of water, the reaction mixture is extracted with methylene chloride. The organic layer is washed with water, dried, and concentrated under reduced pressure. The residue is dissolved in methanol (5 ml), to the solution is added a 1N aqueous solution of sodium hydroxide (20 ml). The mixture is stirred for one hour at room temperature. To the reaction mixture are added ether and water, and the mixture is shaken, then the aqueous layer is separated. The aqueous layer is acidified with concentrated hydrochloric acid, followed by extraction with methylene chloride. The organic layer is concentrated under reduced pressure. The concentrate is dissolved in dioxane (10 ml), to the solution is added concentrated hydrochloric acid. The mixture is stirred for 30 minutes at 100° C. The reaction mixture is extracted with ethyl acetate. The organic layer is washed with water, dried, and concentrated under reduced pressure. The residue is recrystallized from ethyl acetate to afford 8-methoxy-2,3-dihydro-1-benzoxepin-4-carboxylic acid as colorless prisms, m.p. 197°–200° C.

Elemental Analysis for $C_{12}H_{12}O_4$:
Calcd.: C 65.45; H 5.49;
Found: C 65.53; H 5.61.

REFERENCE EXAMPLE 15

A mixture of 1-(3,4,5-trimethoxybenzoyl)piperazine (2.0 g), a Lawesson reagent ([2,4-bis(4-methoxypehnyl)-1,3-dithia-2,4-diphosphethane-2,4-disulfide]) (2.9 g) and benzene (20 ml) is heated under reflux for 30 minutes. After cooling, insolubles are filtered off, and the filtrate is concentrated under reduced pressure. To the residue is added 1N hydrochloric acid (100 ml) and following ethyl acetate (50 ml), and the mixture is shaken. The aqueous layer is separated, and to the aqueous layer is added a 1N aqueous solution of sodium hydroxide to make the system alkaline, followed by extraction with methylene chloride. The organic layer is washed with water and dried, then the solvent is distilled off. The residue is recrystallized from ethyl acetate - hexane to afford 1-(3,4,5-trimethoxythiobenzoyl)piperazine as pale yellow prisms (1.3 g), m.p. 116°–118° C.

Elemental Analysis for $C_{14}H_{20}N_2O_3S.\frac{1}{2}H_2O$:
Calcd.: C 54.26; H 6.99; N 9.04;
Found: C 54.39; H 6.72; N 9.03.

REFERENCE EXAMPLE 16

A mixture of 7,8-dimethyl-3,4-dihydro-1-benzoxepin5(2H)-one (1.3 g), sodium methoxide (2.0 g) and dimethyl carbonate (30 ml) is heated under reflux for 6 hours with stirring. The reaction mixture is treated in a manner as in Reference Example 11 to give methyl 7,8-dimethyl-5-oxo-2,3,4,5-tetrahydro-1-benzoxepin-4-carboxylate as a colorless oily product (1.3 g). This product (1.2 g) is dissolved in a mixture of methylene chloride (40 ml) and methanol (50 ml). To the solution is added sodium borohydride (0.3 g) in limited amounts, and the mixture is stirred. After addition of water, the reaction mixture is extracted with methylene chloride. The organic layers are combined, washed with water, dried, and concentrated under reduced pressure. To the residue are added methanol (2 ml) and a 1N aqueous solution of sodium hydroxide (10 ml). The mixture is stirred at 60° C. for 15 minutes. To the reaction mixture are added water and ether and the mixture is shaken. Then the aqueous layer is separated. The aqueous layer is acidified with dilute hydrochloric acid, followed by extraction with methylene chloride. The organic layers are combined, washed with water, dried, and concentrated under reduced pressure. To the residue are added dioxane (8 ml) and concentrated hydrochloric acid (1 ml). The mixture is stirred at 100° C. for 40 minutes. To the reaction mixture is added water, followed by extraction with ethyl acetate. The organic layer is washed with water, dried, and evaporated to dryness. The residue is recrystallized from ethyl acetate to afford 7,8-dimethyl-2,3-dihydro-1-benzoxepin-4-carboxylic acid as colorless needles (0.75 g), m.p. 266°–267° C.

Elemental Analysis for $C_{13}H_{14}O_3$:
Calcd.: C 71.54; H 6.47;
Found: C 71.33; H 6.36.

WORKING EXAMPLE 1

To a mixture of 1-(3,4,5-trimethoxybenzyl)piperazine (0.5 g), potassium carbonate (3 g), ethyl acetate (30 ml) and water (20 ml) is added dropwise benzoyl chloride (1 ml) at room temperature with stirring. The mixture is stirred for one hour. Ethyl acetate (100 ml) and water (100 ml) are added to the mixture, followed by extraction. The ethyl acetate layer is separated, washed with water, dried, and concentrated under reduced pressure. The residue is dissolved in ethyl ether (200 ml). To the mixture is added hydrogen chloride - ethyl acetate (1N) (4 ml). Resultant precipitates are recrystallized from ethanol - ethyl ether to afford 1-benzoyl-4-(3,4,5-trimethoxybenzyl)piperazine hydrochloride (0.5 g) as colorless powdery crystals, m.p. 220°–225° C. (decomp.).

Elemental Analysis for $C_{21}H_{26}N_2O_4.HCl$:
Calcd.: C 61.99; H 6.69; N 6.88;
Found: C 61.29; H 6.70; N 6.73.

WORKING EXAMPLE 2

To a mixture of 1-(3,4,5-trimethoxybenzyl)piperazine dihydrochloride (0.6 g), sodium bicarbonate (5 g), ethyl acetate (20 ml) and water (20 ml) is added, with stirring at room temperature, 3,4,5-trimethoxybenzoyl chloride (0.61 g), followed by stirring for 30 minutes. The ethyl acetate layer is separated, washed with water, dried, and concentrated under reduced pressure. The residue is dissolved in ethanol (10 ml). To the solution is added a solution of hydrogen chloride - ethanol (1 ml). The mixture is diluted with ethyl ether (100 ml) to give 1-(3,4,5-trimethoxybenzoyl)-4-(3,4,5-trimethoxybenzyl)piperazine hydrochloride (0.6 g) as colorless needles, m.p. 200°–205° C. (decomp.).

Elemental Analysis for $C_{24}H_{32}N_2O_7.HCl.3/2H_2O$:
Calcd.: C 55.01; H 6.93; N 5.35;
Found: C 54.87; H 6.52; N 5.33.

WORKING EXAMPLE 3

A mixture of 3-methoxy-5-nitro-4-propoxybenzoic acid (1 g) obtained in Reference Example 1, toluene (20 ml) and thionyl chloride (2 ml) is heated under reflux for two hours. The reaction mixture is concentrated to dryness under reduced pressure to obtain 3-methoxy-5-nitro-4-propoxy-benzoyl chloride (1 g). A solution of this product dissolved in toluene (20 ml) is added dropwise, at room temperature, to a mixture of 1-(3,4,5-trimethoxybenzyl)piperazine dihydrochloride (1.7 g), triethylamine (4 g) and N,N-dimethyl-formamide (20 ml). The whole mixture is left standing overnight. To the mixture are added water (100 ml) and ethyl acetate (100 ml), followed by extraction. The extract solution is washed with water, dried, and concentrated under reduced pressure. The residue is purified by means of a silica gel column chromatography (hexane:acetone=1:1). The resultant oily product is dissolved in ethyl acetate. To the solution is added 1N hydrogen chloride - ethyl acetate solution (5 ml). The mixture is diluted with ethyl ether to thereby allow 1-(3-methoxy-5-nitro-4-propoxybenzoyl)-4-(3,4,5trimethoxybenzyl)piperazine hydrochloride (1 g) to precipitate as colorless crystals, m.p. 180°–184° C.

Elemental Analysis for $C_{25}H_{33}N_3O_8.HCl.\frac{1}{2}H_2O$:
Calcd.: C 54.69; H 6.43; N 7.65;
Found: C 54.67; H 6.29; N 7.61.

WORKING EXAMPLE 4

A mixture of veratric acid (1.0 g), toluene (10 ml) and thionyl chloride (2 ml) is heated under reflux for one hour, and the reaction mixture is concentrated under reduced pressure. Veratryl chloride thus obtained was dissolved in N,N-dimethylformamide (5 ml). The solution is added dropwise, while stirring under ice-cooling, to a mixture of 1-(3,4,5-trimethoxybenzyl)piperazine dihydrochloride (1.96 g), triethylamine (2.2 g) and N,N-dimethylformamide (8 ml) in the course of 3 minutes, followed by stirring for two hours at room temperature. After addition of water (50 ml), the reaction mixture is extracted twice with ethyl acetate (40 ml each portion). The organic layers are combined, washed with water, dried, and concentrated under reduced pressure. The residue is purified by means of a silica gel column chromatography (eluent, hexane:ethyl acetate:acetone=2:3:1). The oily product thus obtained is dissolved in ethyl acetate (10 ml). To the solution is added a hydrogen chloride-ethanol solution (5N) (1 ml). Resultant precipitates are recrystallized from acetone to afford 1-(3,4-dimethoxybenzoyl)-4-(3,4,5-trimethoxybenzyl)-piperazine hydrochloride (1.6 g) as colorless powdery crystals, m.p. 212°–215° C.

Elemental Analysis for $C_{23}H_{30}N_2O_6 \cdot HCl \cdot 1/5H_2O$:
Calcd.: C 58.71; H 6.73; N 5.95;
Found: C 58.77; H 6.63; N 5.97.

WORKING EXAMPLE 5

A mixture 4-butoxy-3-methoxy-5-nitrobenzoic acid (0.5 g) obtained in Reference Example 2, toluene (6 ml) and thionyl chloride (1.2 ml) is heated under reflux for one hour. The reaction mixture is subjected to distillation under reduced presure to leave 4-butoxy-3-methoxy-5-nitrobenzoyl chloride, which is dissolved in methylene chloride (5 ml). The solution is added dropwise, while stirring under ice-cooling, to a mixture of 1(3,4,5-trimethoxybenzoyl)piperazine hydrochloride (0.65 g), trietylamine (1.0 g) and methylene chloride (10 ml), in the course of 3 minutes, followed by stirring for one hour at room temperature. To the reaction mixture is added water (40 ml), then the methylene chloride layer is separated. The aqueous layer is subjected to extraction with methylene chloride (30 ml). The methylene chloride layers are combined, washed with water, dried, and concentrated under reduced pressure. The residue is purified by means of a silica gel column chromatography (eluent, hexane:ethyl acetate:acetone=2:2:1) to give 1-(4-butoxy-3-methoxy-5-nitrobenzoyl)-4-(3,4,5-trimethoxybenzoyl)piperaxine as crystals (0.85 g). This product is recrystallized from a mixture of ethyl acetate and hexane to give colorless powdery crytals, m.p. 146°–147° C.

Elemental Analysis for $C_{26}H_{33}N_3O_9$:
Calcd.: C 58.75; H 6.26; N 7.91;
Found: C 58.83; H 6.33; N 7.90.

WORKING EXAMPLE 6

To a mixture of 6,7-methylenedioxy-1,2-dihydro-3-naphthoic acid (0.7 g), 1-(3,4,5-trimethoxybenzyl)piperazine dihydrochloride (1.1 g), triethylamine (1.3 g) and N,N-dimethylformamide (20 ml) is added dropwise, while stirring under ice-cooling, diethyl cyanophosphonate (0.8 ml), followed by leaving the system to stand for one hour at room temperature. After addition of water and ethyl acetate, the reaction mixture is extracted with ethyl acetate. The ethyl acetate layer is washed with water, dried, and concentrated under reduced pressure. The residue is purified by means of a silica gel column chromatography. The oily product thus obtained is dissolved in ethyl acetate. To the solution is added hydrogen chloride - ethyl acetate solution (1N) (6 ml) to thereby allow 1-(6,7methyleneidoxy-1,2-dihydro-3-naphthoyl)-4-(3,4,5-trimethoxybenzyl)piperazine hydrochloride to precipitate as colorless prisms (1.2 g), m.p. 235°–240° C. (decomp.).

Elemental Analysis for $C_{26}H_{30}N_2O_6 \cdot HCl$:
Calcd.: C 60.99; H 6.30; N 5.47;
Found: C 60.77; H 6.44; N 5.38.

WORKING EXAMPLE 7

To a mixture of 2-benzofuranecarboxylic acid (0.5 g), 1-(3,4,5-trimethoxybenzyl)piperazine dihydrochloride (1.1 g), triethylamine (1.2 g) and N,N-dimethylformamide (20 ml) is added dropwise, while stirring at room temperature, diethyl cyanophosphonate (1.2 ml), followed by stirring for one hour at room temperature. After addition of water (100 ml), ethyl acetate (100 ml) and hexane (100 ml), the mixture is extracted with ethyl acetate. The organic layer is washed with water, dried, and concentrated under reduced pressure. The residue is purified by means of a silica gel column chromatography (hexane:ethyl acetate:acetone=1:1:0.5) to give an oily product, to which is added 1N hydrogen chloride - ethyl acetate solution (10 ml) to cause precipitation of powder. The powdery product is collected by filtration and recrystallized from a mixture of methanol - ethyl acetate to give 1-(2-benzofuranylcarbonyl)4-(3,4,5-trimethoxybenzyl)piperazine hydrochloride (0.65 g) as colorless needles, m.p. 221°–225° C. (decomp.).

Elemental Analysis for $C_{23}H_{26}N_2O_5 \cdot HCl$:
Calcd.: C 61.81; H 6.09; N 6.27;
Found: C 61.71; H 6.06; N 6.21.

WORKING EXAMPLE 8

To a mixture of 1-(3,4,5-trimethoxybenzyl)piperazine dihydrochloride (1 g), ethyl acetate (50 ml), water (50 ml) and potassium carbonate (3 g) is added, with stirring at room temperature, nicotinoyl chloride hydrochloride (1 g). After stirring for 30 minutes, further nicotinoyl chloride hydrochloride (1 g) is added to the mixture, followed by stirring for another one hour. The ethyl acetate layer is separated, washed with an aqueous solution of sodium bicarbonate and water, successively, and dried, then the solvent is distilled off under reduced pressure. The residue is dissolved in a mixture of ethanol and ethyl acetate. To the mixture is added a 1N hydrogen chloride - ethyl acetate solution (10 ml). The mixture is diluted with ethyl ether, then precipitating powder is collected by filtration to yield 1-(nicotinoyl)-4-(3,4,5-trimethoxybenzoyl)piperazine dihydrochloride (0.8 g) as colorless powder.

Elemental Analysis for $C_{20}H_{25}N_3O_4 \cdot 2HCl \cdot 3H_2O$:
Calcd.: C 48.20; H 6.67; N 8.43;
Found: C 47.95; H 6.33; N 8.00.

WORKING EXAMPLE 9

To a mixture of benzothiazole-2-carboxylic acid (0.1 g), 1-(3,4,5-trimethoxybenzyl)piperazine dihyirochloride (0.3 g), triethylamine (0.4 g) and N,N-dimethylformamide (5 ml) is added dropwise, while stirrign at room temperature, diethyl cyanophosphonate (0.2 ml). The mixture is stirred for 4 hours. After addition of water (100 ml), the mixture is extracted twice with 50 ml each portion of ethyl acetate. The extract is dried and concentrated under reduced pressure. The residue is purified by means of a silica gel column chromatography (hexane:acetone=2:1). The resultant oily product is dissolved in ethyl acetate. To the solution is added a 1N hydrogen chloride - ethyl acetate solution (1 ml). The mixture is diluted with petroleum ether, then resulting precipitates are collected by filtration to afford 1-(2- benzothaizolylcarbonyl)-4-(3,4,5-trimethoxybenzyl)-piperazine hydrochlorde (0.05 g) as colorless prisms, m.p. 219°-221° C. (decomp.).

Elemental Analysis for $C_{22}H_{25}N_3O_4S.HCl.H_2O$:
Calcd.: C 54.82; H 5.86; N 8.72;
Found: C 54.91; H 5.61; N 8.61.

WORKING EXAMPLE 10

To a mixture of thiophene-2-carboxylic acid (0.4 g), 1-(3,4,5-trimethoxybenzyl)piperazine dihydrochloride (1.1 g), triethylamine (1.2 g) and dimethylformamide (20 ml) is added dropwise, while stirring, diethyl cyanophosphonate (1.2 ml), followed by stirring for one hour. To the reaction mixture are added water (100 ml) and ethyl acetate (100 ml), followed by extraction. The extract is washed with water, dried and concentrated under reduced pressure. The residue is purified by means of a silica gel column chromatography (hexane:acetone=2:1) to give an oily product, which is led to its hydrochloride in a mixture of ethyl acetate - ethyl ether to yield 1-(2-thenoyl)-4-(3,4,5-trimethoxybenzyl)-piperazine hydrochloride (0.65 g) as colorless needles, m.p. 205°-209° C. (decomp.).

Elemental Analysis for $C_{19}H_{24}N_2O_4S.HCl$:
Calcd.: C 55.26; H 6.10; N 6.78;
Found: C 55.15; H 6.11; N 6.72.

WORKING EXAMPLE 11

To a mixture of 2-quinolinecarboxylic acid (0.55 g), 1-(3,4,5-trimethoxybenzyl)piperazine dihydrochloride (1.1 g), triethylamine (1.2 g) and N,N-dimethylformamide (20 ml) is added dropwise at room temperature diethyl cyanophosphonate (1.2 ml), followed by stirring for one hour. After addition of water (100 ml) and ethyl acetate (100 ml), the reaction mixture is extracted with ethyl acetate. The extract is washed with water, dried, and concentrated under reduced pressure. The residue is purified by means of a silica gel column chromatography (hexane:acetone=2:1-1:1) to give an oily product, which is led to its hydrochloride, followed by crystallizing from a mixture of methanol, ethyl acetate and ethyl ether to give 1-(2-quinolylcarbonyl)-4-(3,4,5-trimethoxybenzyl)piperazine dihydrochloride (0.4 g) as colorless crystals, m.p. 151°-155° C.

Elemental Analysis for $C_{24}H_{27}N_3O_4.2HCl.\frac{1}{2}H_2O$:
Calcd.: C 57.26; H 6.01; N 8.35;
Found: C 57.70; H 5.81; N 8.37.

WORKING EXAMPLE 12

To a mixture of coumarin-3-carboxylic acid (0.9 g), 1(3,4,5-trimethoxybenzyl)piperazine dihydrochloride (1.7 g), triethylamine (1.8 g) and N,N-dimethylformamide (20 ml) is added dropwise at room temperature diethyl cyanophosphonate (1.8 ml), followed by stirring for one hour. After addition of water (50 ml), the reaction mixture is left standing for 30 minutes, followed by addition of water (150 ml), ethyl acetate (200 ml) and hexane (50 ml). The mixture is vigorously mixed and the organic layer is separated. The organic layer is washed with water, dried, and concentrated under reduced pressure. The residue is purified by means of a silica gel column chromatography(hexane:acetone=1:1-1:2) to give an oily product, which is crystallized from a mixture of acetone and ethyl ether to afford 1-(3-coumarinylcarbonyl)-4-(3,4,5-trimethoxybenzyl)piperazine (0.35 g) as colorless needles, m.p. 171°-173° C.

Elemental Analysis for $C_{24}H_{26}N_2O_6$:
Calcd.: C 65.74; H 5.98; N 6.39;
Found: C 65.48; H 5.97; N 6.26.

WORKING EXAMPLE 13

To a mixture of 3-thiophenecarboxylic acid (0.2 g), 1(3,4,5-trimethoxybenzyl)piperazine dihydrochloride (0.56 g), triethylamine (0.6 g) and N,N-dimethylforamide (10 ml) is added dropwise at room temperature diethyl cyanophosphonate (0.6 ml), followed by stirring for one hour. After addition of water (100 ml) and ethyl acetate (100 ml), the reaction mixture is extracted with ethyl acetate. The extract is washed with water, dried, and concentrated under reduced pressure. The residue is purified by means of a silica gel column chromatography(hexane:acetone=2:1) to give an oily product, which is led to its hydrochloride, followed by crystallization from a mixture of ethyl acetate and ethyl ether to afford 1-(3-thenoyl)-4-(3,4,5-trimethoxybenzyl)piperazine hydrochloride (0.3 g) as colorless needles, m.p. 201°-205° C. (decomp.).

Elemental Analysis for $C_{19}H_{24}N_2O_4S.HCl$:
Calcd.: C 55.26; H 6.10; N 6.78;
Found: C 55.42; H 6.08; N 6.72.

WORKING EXAMPLE 14

To a mixture of indole-5-carboxylic acid (1 g), 1-(3,4,5-trimethoxybenzyl)piperazine dihydrochloride (2.2 g), triethylamine (1.9 g) and N,N-dimethylformamide (20 ml) is added dropwise under ice-cooling diethyl cyanophosphonate (1.5 ml), followed by stirring for 30 minutes under ice-cooling and for further one hour at room temperature. After addition of water (200 ml), ethyl acetate (200 ml) and hexane (50 ml), the reaction mixture is extracted with ethyl acetate. The extract is washed with water, dried, and concentrated. The residue is purified by means of a silica gel column chromatography(hexane:acetone=1:1) to give 1-(5-indolylcarbonyl)-4-(3,4,5-trimethoxybenzyl)piperazine (1.9 g) as a colorless oily product. This product (0.3 g) is led to its fumarate in ethyl ether to obtain colorless powder (0.25 g).

Elemental Analysis for $C_{23}H_{27}N_3O_4.C_4H_4O_4.\frac{1}{2}H_2O$:
Calcd.: C 60.67; H 6.03; N 7.86;
Found: C 60.54; H 6.29; N 7.65.

WORKING EXAMPLE 15

A mixture of isonicotinic acid (2 g) and thionyl chloride (10 ml) is stirred for 1.5 hour at 80° C. The reaction mixture is cooled, and diluted with toluene (50 ml). Then precipitating crystals are collected by filtration. This product is added, while stirring at room temperature in limited amounts, to a mixture of 1(3,4,5-trimethoxybenzyl)piperazine dihydrochloride (1.0 g), ethyl acetate (100 ml), water (50 ml) and sodium bicarbonate (10 g), followed by stirring for two hours. The ethyl acetate layer is separated, washed with water, dried, and concentrated under reduced pressure. The residue is dissolved in ethyl acetate. To the solution is added a 1N hydrogen chloride - ethyl acetate solution (10 ml), followed by collecting then resultant precipitates by filtration to give 1-isonicotinoyl-4-(3,4,5-trimethoxybenzyl)piperazine dihydrochloride (0.8 g) as colorless powder.

Elemental Analysis for $C_{20}H_{25}N_3O_4.2HCl.2H_2O$:
Calcd.: C 50.01; H 6.50; N 8.75;
Found: C 49.79; H 6.64; N 8.50.

WORKING EXAMPLE 16

A mixture of 3-quinolinecarboxylic acid (0.7 g) and thionyl chloride is refluxed for one hour. After cooling, benzene (100 ml) is added to the reaction mixture, then precipitating crystals are collected by filtration. This product is added to a mixture of 1-(3,4,5-trimethoxybenzyl)piperazine dihydrochloride (1.5 g), triethylamine(2.2 g) and dimethylacetamide (20 ml), followed by stirring at room temperature for 30 minutes. To the reaction mixture are added water (100 ml), ethyl acetate (200 ml) and hexane (50 ml), then extraction is conducted. The extract is washed with water, dried, and concentrated under reduced pressure. The residue is purified by means of a silica gel column chromatography(hexane:acetone=2:3–1:2) to give a colorless oily product. This product is dissolved in ethyl acetate. The solution is treated with hydrogen chloride to afford 1-(3-quinolylcarbonyl)-4-(3,4,5-trimethoxybenzyl)piperazine dihydrochloride (1.1 g) as colorless powder.

Elemental Analysis for $C_{24}H_{27}N_3O_4.2HCl.5/2H_2O$:
Calcd.: C 53.44; H 6.35; N 7.79;
Found: C 53.37; H 6.02; N 7.80.

WORKING EXAMPLE 17

A mixture of 1,4-benzodioxane-6-carboxylic acid (0.5 g), benzene (20 ml) and thionyl chloride (5 ml) is heated for one hour under reflux. The reaction mixture is evaporated to dryness under reduced pressure. To the residue is added benzene (50 ml), then the solvent is again distilled off to leave 1,4-benzodioxane-6-carbonyl chloride. This compound dissolved in benzene (20 ml) is added dropwise, while stirring, to a mixture of 1-(3,4,5trimethoxybenzyl)piperazine dihydrochloride (1 g), triethylamine (1.5 g) and N,N-dimethylacetamide (20 ml), followed by stirring at room temperature for 30 minutes. To the reaction mixture are added water (100 ml), ethyl acetate (200 ml) and hexane (50 ml), then extraction is conducted. The extract is washed with water, dried, and concentrated under reduced pressure. The residue as purified by means of a silica gel column chromatography (hexane:acetone=1:1–2:3) to afford an oily product, which is dissolved in ethyl acetate. To the solution is added 1N hydrogen chloride - acetic acid solution (5 ml), and the mixture is left standing. The supernatant is removed by decantation, and the precipitates are recrystallized from ethyl acetate to give 1-(1,4-benzodioxan-6-ylcarbonyl)-4-(3,4,5-trimethoxybenzyl)piperazine hydrochloride (0.7 g) as colorless prisms, m.p. 180°–185° C.

Elemental Analysis for $C_{23}H_{28}N_2O_6HCl\frac{1}{2}H_2O$:
Calcd.: C 58.29; H 6.38; N 5.91;
Found: C 58.35; H 6.36; N 5.79.

WORKING EXAMPLE 18

To a mixture of 7-methoxy-3,4-dihyirobenzofuran-2-carboxylic acid (0.7 g) obtained in Reference Example 4, 1-(3,4,5-trimethoxybenzyl)piperazine dihydrochloride (1.02 g), triethylamine (1.15 g) and N,N-dimethylformamide (20 ml) is added dropwise, under ice-cooling, diethyl cyanophosphonate (1 ml), followed by stirring for one hour. To the reaction mixture are added water (100 ml), ethyl acetate (200 ml) and hexane (50 ml), then extraction is conducted. The extract is washed with water, dried, and concentrated under reduced pressure. The residue is purified by means of a silica gel column chromatography (hexane:acetone=1:1) to give an oily product. The product is dissolved in ethyl acetate. To the solution is added a 1N hydrogen chloride - ethyl acetate solution (10 ml). The mixture is diluted with ethyl ether, and then precipitating crystals are collected by filtration to give 1-(7-methoxy-3,4-dihydrodibenzofuran-2-ylcarbonyl)-4-(3,4,5-trimethoxybenzyl)piperazine hydrochloride (1.3 g) as pale yellow prisms, m.p. 220°–225° C. (decomp.).

Elemental Analysis for $C_{28}H_{32}N_2O_6.HCl$:
Calcd.: C 63.57; H 6.29; N 5.30;
Found: C 63.14; H 6.30; N 5.15.

WORKING EXAMPLE 19

To a mixture of 1-hydroxy-1,2,3,4-tetrahydro-2-dibenzothiophenecarboxylic acid (0.7 g) obtained in Reference Example 5, 1-(3,4,5-trimethoxybenzyl)piperazine dihydrochloride (1.1 g), triethylamine (1.2 g) and N,N-dimethylformamide (20 ml) is added dropwise diethyl cyanophosphonate (1 ml), followed by stirring under ice-cooling for one hour. To the reaction mixture are added water (100 ml), ethyl acetate (200 ml) and hexane (50 ml), then extraction is conducted. The extract is washed with water, dried, and evaporated to dryness. The residue is purified by means of a silica gel column chromatography (hexane:acetone=1:1–1:2) to give an oily product, which is led to its hydrochloride in ethyl acetate, then precipitating powder is collected by filtration, followed by recrystallization from a mixture of methanol and ethyl ether to give 1-(1-hydroxy-1,2,3,4-tetrahydrodibenzothiophen-2-ylcarbonyl)-4-(3,4,5-trimethoxybenzyl)piperazine hydrochloride (0.5 g) as colorless crystals, m.p. 193°–195° C.

Elemental Analysis for $C_{27}H_{32}N_2O_5S.HCl.\frac{1}{2}H_2O$:
Calcd.: C 59.82; H 6.32; N 5.17;
Found: C 59.81; H 6.21; N 5.15.

WORKING EXAMPLE 20

To a mixture of 3,4-dihydro-2-dibenzothiophenecarboxylic acid (0.7 g) obtained in Reference Example 6, 1(3,4,5-trimethoxybenzyl)piperazine dihydrochloride (1.1 g), triethylamine (1.2 g) and N,N-dimethylformamide (20 ml) is added dropwise under ice-cooling diethyl cyanophosphonate (1 ml), followed by stirring for one hour under ice-cooling. After addition of water (100 ml), ethyl acetate (200 ml) and hexane (50 ml), the reaction mixture is extracted with ethyl acetate. The extract is washed with water, dried, and concentrated under reduced pressure. The residue is purified by means of a silica gel column chromatography (hexane:acetone=1:1–1:2) to give an oily product. This product is then led to its hydrochloride in ethyl acetate to thereby allow 1-(3,4-dihydrodibenzothiophen-2-ylcarbonyl)4-(3,4,5-trimethoxybenzyl)piperazine hydrochloride to precipitate as colorless prisms (1.4 g), m.p. 220°–225° C. (decomp.)

Elemental Analysis for $C_{27}H_{30}N_2O_4.HCl$:
Calcd.: C 62.96; H 6.07; N 5.44;
Found: C 62.73; H 6.09; N 5.39.

WORKING EXAMPLE 21

To a mixture of 3-oxospiro[benzofuran-2(3H),1'-cyclopropane]-5-carboxylic acid [Kawada et al., Chem. Pharm. Bull., 32, 3532(1984)] (1.0 g), 1-(3,4,5-trimethoxybenzyl)piperazine dihydrochloride (1.83 g), triethylamine (1.98 g) and N,N-dimethylformamide (12 ml) is added dropwise under ice-cooling diethyl cyanophosphonate (1.04 g), followed by stirring at room temperature for one hour. To the reaction mixture are added water (100 ml) and ethyl acetate (100 ml), then extraction is conducted. The extract is washed with water, dried, and concentrated under reduced pressure. The residue is purified by means of a silica gel column chromatography (hexane:ethyl acetate:methanol=10:15:1) to give an oily product. This product is crystallized from ethyl acetate to afford 1-[3-oxospiro[benzofuran-2(3H), 1,-cyclopropan]-5-ylcarbonyl]-4-(3,4,5-trimethoxybenzyl)piperazine (1.5 g) as colorless crystals, m.p. 144°–145° C.

Elemental Analysis for $C_{25}H_{28}N_2O_6 \cdot C_4H_4O_4$:
Calcd.: C 66.36; H 6.24; N 6.19;
Found: C 66.30; H 6.27; N 6.21.

This product (0.7 g) is dissolved in methanol (10 ml), in which is dissolved fumaric acid (0.18 g), followed by concentration under reduced pressure. The concentrate is crystallized from ethanol to give 1-[3-oxospiro[benzofuran2(3H), 1'-cyclopropan]-5-ylcarbonyl]-4-(3,4,5-trimethoxybenzyl)piperazine.fumarate (0.6 g) as colorless needles, m.p. 196°–198° C.

Elemental Analysis for $C_{25}H_{28}N_2O_6 \cdot C_4H_4O_4$:
Calcd.: C 61.26; H 5.67; N 4.93;
Found: C 61.25; H 5.72; N 4.92.

WORKING EXAMPLE 22

In a mixture of methylene chloride (2 ml) and methanol (10 ml) is dissolved 1-[3-oxospiro[benzofuran-2(3H), 1'-cyclopropan]-5-ylcarbonyl]-4-(3,4,5-trimethoxybenzyl)piperazine (0.5 g). To the solution is added, while stirring under ice-cooling, sodium borohydride (0.2 g). The reaction mixture is concentrated under reduced pressure. After addition of water (50 ml), the residue is extracted with ethyl acetate. The extract is washed with water, dried, and concentrated to give 1-[3-hydroxyspiro[benzofuran-2(3H), 1'-cyclopropan]-5-ylcarbonyl]-4-(3,4,5-trimethoxybenzyl)piperazine (0.48 g) as a colorless oily product. This product (0.15 g) and fumaric acid (0.04 g) are dissolved in methanol (3 ml). The mixture is concentrated under reduced pressure. To the concentrate is added ether to give 1-[3-hydroxyspiro[benzofuran-2(3H), 1'-cyclopropan]-5-ylcarbonyl]-4-(3,4,5-trimethoxybenzyl)piperazine-fumarate (0.13 g) as a powdery product.

Elemental Analysis for $C_{25}H_{30}N_2O_6 \cdot C_4H_4O_4 \cdot \frac{1}{2}H_2O$:
Calcd.: C 60.10; H 6.09; N 4.83;
Found: C 60.07; H 6.26; N 4.52.

WORKING EXAMPLE 23

In toluene (7 ml) is dissolved 7,8-dimethoxy-2,3-dihydro-1-benzothiepin-4-carboxylic acid (1.0 g). To the solution is added thionyl chloride (4.0 g), and the mixture is stirred for one hour at 100° C. The reaction mixture is concentrated under reduced pressure to give a crude product of acid chloride. A solution of the crude acid chloride dissolved in methylene chloride (5 ml) is added dropwise, while stirring at 0° C., to a solution of 1-(3,4,5-trimethoxybenzyl)piperazine dihydrochloride (1.6 g) in a mixture of triethylamine (2.5 ml) and methylene chloride (10 ml). The reaction mixture is stirred for 20 minutes at 0° C. then for further 20 minutes at room temperature. The reaction mixture is poured into an aqueous solution of sodium hydrogencarbonate, followed by extraction with methylene chloride. The organic layer is washed with water, dried, and evaporated to dryness. The residue is purified by means of a silica gel column chromatography to give 1-(7,8-dimethoxy-2,3-dihydro-1-benzothiepin-4-carbonyl)-4-(3,4,5-trimethoxybenzyl)piperazine as a colorless oily product (1.8 g). This product is converted into its hydrochloride, followed by recrystallization from ethanol to give colorless crystals, m.p. 187°–189° C.

Elemental Analysis for $C_{27}H_{34}N_2O_6S \cdot HCl \cdot \frac{1}{2}H_2O$:
Calcd.: C 57.90; H 6.48; N 5.00;
Found: C 58.33; H 6.44; N 4.97.

WORKING EXAMPLE 24

7,8-Dimethoxy-2,3-dihydro-1-benzothiepin-4-carboxylic acid (1.0 g) obtained in Reference Example 9 is stirred for one hour at 100° C. together with thionyl chloride (4.0 g) and toluene (7 ml). The reaction mixture is concentrated under reduced pressure to give a crude acid chloride, which is dissolved in methylene chloride. This solution is added dropwise, while stirring at room temperature, to a solution of 1-(3,4,5-trimethoxybenzoyl)piperazine hydrochloride (1.6 g) in a mixture of triethylamine (2.5 ml) and methylene chloride (10 ml), followed by stirring for two hours. The reaction mixture is then poured into ice-water containing dilute hydrochloric acid, followed by extraction with methylene chloride. The organic layer is washed with an aqueous solution of sodium hydrogencarbonate, dried, and concentrated under reduced pressure. The residue is purified by means of a silica gel column chromatography (eluent:ethyl acetate), followed by recrystallization from ethanol-ether (1:1) to afford 1-(7,8-dimethoxy-2,3-dihydro-1-benzothiepin-4-carbonyl)-4-(3,4,5 -trimethoxybenzoyl)piperazine as colorless prisms (2.0 g), m.p. 113° C.

Elemental Analysis for $C_{27}H_{32}N_2O_7S$:
Calcd.: C 61.35; H 6.10; N 5.30;
Found: C 61.48; H 6.20; N 5.24.

WORKING EXAMPLE 25

To a solution of 7,8-dimethoxy-2,3-dihydro-1-benzoxepin-4-carboxylic acid (0.5 g) dissolved in toluene (10 ml) is added thionyl chloride (1.5 ml), followed by stirring for one hour at 100° C. The reaction mixture is concentrated under reduced pressure to give a crude acid chloride, which is dissolved in methylene chloride (8 ml). The solution is added dropwise, while stirring under ice-cooling, to a solution of 1-(3,4,5-trimethoxybenzyl)piperazine (0.78 g) in a mixture of methylene chloride (20 ml) and triethylamine (1.6 ml), followed by stirring for 3 hours. The reaction mixture is poured into ice-water, followed by extraction with methylene chloride. The organic layer is washed with water, dried, and concentrated under reduced pressure. The residue is purified by means of a silica gel column chromatography (eluent: hexane-acetone-ethanol=10:8:1) to afford 1-(7,8-dimethoxy-2,3-dihydro-1-benzoxepin-4-carbonyl)-4-(3,4,5-trimethoxybenzyl)piperazine as a colorless oily product (0.9 g). This product is converted into its hydrochloride, followed by recrystallization from ethanol-ether to give colorless needles, m.p. 208°–210° C.

Elemental Analysis for $C_{27}H_{34}N_2O_7 \cdot HCl \cdot \frac{1}{2}H_2O$:
Calcd.: C 59 61; H 6.67; N 5.15;
Found: C 60.00; H 6.57; N 5.20.

WORKING EXAMPLE 26

7,8-Dimethoxy-2,3-dihydro-1-benzoxepin-4-carboxylic acid (0.5 g) obtained in Reference Example 12 is stirred at 100° C. for one hour together with toluene (10 ml) and thionyl chloride (1.5 ml). The reaction mixture is concentrated under reduced pressure to give a crude product of acid chloride. A solution of the crude acid chloride dissolved in methylene chloride (8 ml) is added dropwise, while stirring under ice-cooling, to a solution of 1-(3,4,5trimethoxybenzoyl)piperazine hydrochloride (0.7 g) in a mixture of methylene chloride (18 ml) and triethylamine (1.2 ml). The reaction mixture is stirred for two hours and poured into ice-water; this is followed by extraction with methylene chloride. The organic layer is washed with water, dried, and concentrated under reduced pressure. The residue is purified by means of a silica gel column chromatography (eluent:hexane - ethyl acetate - ethanol=10:15:2) to afford 1-(7,8-dimethoxy-2,3-dihydro-1-benzoxepin-4-carbonyl)-4-(3, 4,5-trimethoxybenzoyl)piperazine as crude crystals (1.0 g), followed by recrystallization from ethyl acetate - hexane to give colorless needles, m.p. 132°–134° C.

Elemental Analysis for $C_{27}H_{32}N_2O_8$:
Calcd.: C 63.27; H 6.29; N 5.47;
Found: C 63.23; H 6.39; N 5.34.

WORKING EXAMPLE 27

To a mixture of 7-methoxy-2,3-dihydro-1-benzoxepin-4-caboxylic acid (0.3 g) obtained in Reference Example 13, 3,4,5-trimethoxybenzoylpiperazine (0.38 g) and N,N-dimethylformamide (5 ml) are added, while stirring under ice-cooling, triethylamine (0.3 ml) and then diethylcyanophosphonate (0.33 g), followed by stirring for 30 minutes. The reaction mixture is then stirred at room temperature for one hour, poured into ice-water, and extracted with ethyl acetate. The organic layer is washed with water, dried, and concentrated under reduced pressure. The residue is purified by means of a silica gel column chromatography (eluent:hexane - ethyl acetate - ethanol=20:20:3). The resultant crude product is recrystallized from acetone to afford 1-(7-methoxy-2,3-dihydro-1benzoxepin-4-carbonyl)-4-(3,4,5-trimethoxybenzoyl)piperazine as colorless needles (0.52 g), m.p. 110°–115° C.

Elemental Analysis for $C_{26}H_{30}N_2O_7 \cdot \frac{1}{2}H_2O$:
Calcd.: C 63.53; H 6.36; N 5.70;
Found: C 63.79; H 6.16; N 5.61.

WORKING EXAMPLE 28

A mixture of 8-methoxy-2,3-dihydro-1-benzoxepin-4carboxylic acid (0.6 g) obtained in Reference Example 14, toluene (10 ml) and thionyl chloride (1.0 ml) is stirred at 110° C. for one hour. The reaction mixture is concentrated under reduced pressure to give a crude product of 8-methoxy-2,3-dihydro-1-benzoxepin-4-carbonyl chloride. Thus-obtained acid chloride is dissolved in methylene chloride. The solution is added dropwise, while stirring under ice-cooling, to a mixture of 1-(3,4,5-trimethoxybenzoyl)piperazine (0.92 g), triethylamine (1.2 ml) and methylene chloride (15 ml); this is followed by stirring for one hour at room temperature. After addition of water, the mixture is shaken. The organic layer is separated and concentrated under reduced pressure. The concentrate is dissolved in ethyl acetate (60 ml), then the organic layer is washed with successive, dilute hydrochloric acid, an aqueous solution of sodium hydrogencarbonate and water. The resultant is dried, followed by distilling off the solvent under reduced pressure. To the residue is added ether to cause crystallization, then crude crystals are collected by filtration, followed by recrystallization from ethyl acetate hexane to give 1-(8-methoxy-2,3-dihydro-1-benzoxepin-4-carbonyl)-4-(3,4,5-trimethoxybenzoyl)piperazine as colorless needles (0.95 g), m.p. 133°–135° C.

Elemental Analysis for $C_{26}H_{30}N_2O_7$:
Calcd.: C 64.72; H 6.27; N 5.81;
Found: C 64.80; H 6.20; N 5.56.

WORKING EXAMPLE 29

A mixture of 7,8-dimethoxy-2,3-dihydro-1-benzoxepin4-carboxylic acid (0.4 g) obtained in Reference Example 12, toluene (10 ml) and thionyl chloride (1.0 ml) is stirred at 100° C. for one hour. The reaction mixture is concentrated under reduced pressure to give a crude 7,8-dimethoxy-2,3-dihydro-1-benzoxepin-4-carbonyl chloride. The crude product is dissolved in methylene chloride (10 ml). The solution is added dropwise, while stirring under ice-cooling, to a mixture of 1-(3,4,5-trimethoxythiobenzoyl)piperazine (0.45 g), triethylamine (0.8 ml) and methylene chloride (20 ml); this is followed by stirring at room temperature for 3 hours. After addition of water, the mixture is shaken, and the organic layer is separated and concentrated under reduced pressure. The residue is dissolved in ethyl acetate (60 ml), and the organic layer is washed with successive, dilute hydrochloric acid, an aqueous solution of sodium hydrogencarbonate and water, and then dried. The solvent is distilled off under reduced pressure, and the residue is chromatography(eluent:hexane - ethyl acetate - ethanol=15:10:1) to give 1-(7,8-dimethoxy2,3-dihydro-1-benzoxepin-4-carbonyl)-4-(3,4,5-trimethoxythiobenzoyl)piperazine as yellow powder (0.72 g).

Elemental Analysis for $C_{27}H_{32}N_2O_7S$:
Calcd.: C 60.32; H 6.19; N 5.21;
Found: C 60.27; H 6.23; N 4.93.

WORKING EXAMPLE 30

In methanol (10 ml) is dissolved 1-(7,8-dimethoxy-2,3-dihydro-1-benzothiepin-4-carbonyl)-4-(3,4,5-trimethoxybenzoyl)piperazine (1.6 g) obtained in Working Example 24. To the solution is added dropwise, while stirring under ice-cooling, a solution of sodium periodate (960 mg) in water (1 ml). The mixture is stirred for one hour under ice-cooling, and left standing for 48 hours at −5° C. Resultant precipitates are filtered off. To the filtrate is added water, followed by extraction with methylene chloride. The organic layer is washed with an aqueous solution of sodium hydrogencarbonate, dried, and concentrated under reduced pressure. The residue is recrystallized from ethanol-ether to give 1-(7,8-dimethoxy-1-oxo-2,3-dihydro1-benzothiepin-4-carbonyl)-4-(3,4,5-trimethoxybenzoyl)piperazine as colorless prisms (1.3 g), m.p. 138° C.

Elemental Analysis for $C_{27}H_{32}N_2O_8S \cdot \frac{1}{2}H_2O$:
Calcd.: C 58.57; H 6.01; N 5.06;
Found: C 58.35; H 5.87; N 4.90.

WORKING EXAMPLE 31

In methylene chloride (10 ml) is dissolved 1-(7,8-dimethoxy-2,3-dihydro-1-benzothiepin-4-carbonyl)-4-(3,4,5-trimethoxybenzoyl)piperazine (1.6 g) obtained in Working Example 24. To the solution is added, while stirring under ice-cooling, m-chloro-perbenzoic acid (1.71 g) in limited amounts. The mixture is stirred for one hour, and then left standing at −5° C. for 15 hours. To the reaction mixture is added an aqueous solution of acid sodium sulfite to decompose the excess peracid. The resultant is poured into an aqueous solution of sodium hydrogencarbonate; this is followed by extraction with methylene chloride. The organic layer is washed with an aqueous solution of sodium hydrogencarbonate, dried, and concentrated under reduced pressure. The residue is recrystallized from ethanol to give 1-(7,8-dimethoxy-1,1-dioxo-2,3-dihydro-1-benzo-thiepin4-carbonyl)-4-(3,4,5-trimethoxybenzoyl)piperazine as colorless prisms (1.4 g), m.p. 226°–229° C.
Elemental Analysis for $C_{27}H_{32}N_2O_9S \cdot H_2O$:
Calcd.: C 56.04; H 5.92; N 4.84;
Found: C 56.34; H 5.67; N 4.78.

WORKING EXAMPLE 32

A mixture of 7,8-dimethyl-2,3-dihydro-1-benzoxepin-4carboxylic acid (0.5 g) obtained in Reference Example 16, toluene (10 ml) and thionyl chloride (1 ml) is stirred at 100° C. for one hour. The reaction mixture is concentrated under reduced pressure to give a crude product of acid chloride. The crude acid chloride is dissolved in methylene chloride (6 ml). The solution is added dropwise, while stirring under ice-cooling, to a solution of 1-(3,4,5trimethoxybenzoyl)piperazine (0.77 g) in methylene chloride (15 ml) and triethylamine (1 ml). The reaction mixture is stirred for 2 hours, and poured into ice-water, followed by extraction with methylene chloride. The organic layer is washed with water and dried, then the solvent is distilled off under reduced pressure. The residue is purified by means of a silica gel column chromatography (eluent:hexane - ethyl acetate - ethanol=10:10:1) to yield crude crystals (1.0 g) of 1-(7,8-dimethyl-2,3-dihydro-1-benzoxepin-4-carbonyl)-4-(3,4,5-trimethoxybenzoyl)piperazine, followed by recrystallization from ethyl acetate - hexane to afford colorless needles, m.p. 177°–178° C.
Elemental Analysis for $C_{27}H_{32}N_2O_6$:
Calcd.: C 67.48; H 6.71; N 5.83;
Found: C 67.25; H 6.75; N 5.72.

WORKING EXAMPLE 33

A mixture of 1-(7,8-dimethoxy-2,3-dihydro-1-benzoxepin4-ylcarbonyl)-4-(3,4,5-trimethoxybenzoyl)piperazine obtained in Working Example 26 (0.5 g) and methanol (20 ml) is stirred under a hydrogen stream in the presence of 10% palladium-carbon (0.3 g) under atmospheric pressure at room temperature for 10 hours. After filtration of the catalyst, the filtrate is concentrated under reduced pressure. The residue is dissolved in ethyl acetate. The resulting solution is washed with water, dried and concentrated in vacuo. The residue is tritutated with ethyl ether and the resulting powder is filtered off to give 1-(7,8-dimethoxy2,3,4,5-tetrahydro-1-benzoxepin-4-ylcarbonyl)-4-(3,4,5-trimethoxybenzoyl)piperazine as a colorless powder (0.4 g).
Elemental Analysis for $C_{27}H_{34}N_2O_8 \cdot H_2O$:
Calcd.: C 60.89; H 6.81; N 5.26;
Found: C 60.59; H 6.51; N 5.00.

(Effects of the Invention)

The compounds (I) of the present invention and their salts are excellent in absorption from the intestinal canal and show excellent PAF antagonism even by oral administration. Therefore, the compounds (I) and their salts can be administered not only non-orally such as by injection, but also orally.

The following test examples explain the effects of the present invention in a more concrete manner.

TEST EXAMPLE 1

Inhibitory action on PAF-induced platelet aggregation

Blood was collected from the hearts of conscious New Zealand white male rabbits weighing 2 to 3 Kg using citric acid as an anticoagulant (one volume part of 3.15% citric acid relative to 9 volume parts of the whole blood). The blood was subjected to a centrifuge at 800 rpm for 10 minutes to obtain platelet rich plasma (PRP). The remaining blood after collecting the PRP was subjected to a centrifuge at 3000 rpm for 10 minutes to obtain platelet poor plasma (PPP). PRP was diluted with PPP to adjust the number of platelets to about 500,000/µl. Platelet aggregation was examined by means of turbidimetry [Born, Nature, 194, 927–929 (1962)] with 8 channel aggregometer (NBS HEMA TRACER 6 Nikoh, Bio-science, Japan). More concretely, PRP (250µl) was kept warm (37° C.) for 3 minutes in a silicon-processed cuvette, to which was added a test sample (25µl) dissolved in a physiological saline or in 10mM dimethlsulfoxide followed by dilution with a physiological saline. Two minutes later, PAF (25µl, $3 \times 10^{-9} - 1 \times 10^{-8} M$), dissolved in a physiological saline, was added and then the maximum aggregation rate was determined. As the control, physiological saline without test sample was added to the cuvette, and the inhibitory rate thereon was determined.

The results are shown in Table 1.
Incidentally, Compound B means N,N'-bis(3,4,5-trimethoxybenzoyl)piperazine (a known compound).

TABLE 1

| No. of Working Example corresponding to test compound | Platelet Aggregation Inhibitory Action (%) (Concentration of test compound: $3 \times 10^{-5}$ M) |
|---|---|
| 2 | 100 |
| 3 | 100 |
| 6 | 93 |
| 8 | 63 |
| 9 | 52 |
| 12 | 78 |
| 13 | 46 |
| 16 | 58 |
| 17 | 88 |
| 18 | 84 |
| 19 | 64 |
| 21 | 100 |
| 22 | 100 |
| 23 | 74 |
| 24 | 100 |
| 25 | 100 |
| 26 | 100 |
| 33 | 47 |
| 7 | 74 |
| B | 100 |

TEST EXAMPLE 2

Inhibitory action on PAF-induced hypotension

SD (Jcl) male rats of 6 to 8 week old were applied with cannulation into the femoral artery and vein under anesthesia with pentobarbital. The animals were fasted overnight, then subjected to the experiment. A tansducer (MPU-0.5-290-0-III, TOYO BALDWIN, Japan) was connected with the artery cannula, and blood pressure was continuously measured by means of polygraph (San-ei, Japan). When the blood pressure became constant, PAF (0.5 to 1.0 µg/kg, 250 µl/kg) dissolved in a physiological saline was injected through the venous cannula to lower the blood pressures by 30 to 45 mmHg. Thirty minutes later, PAF was injected again, and the average of lowered values of blood pressure (twice) was used as the control. After restoration of blood pressure to the initial level, test samples prepared by dissolving or suspending the drug in a physiological saline suspension of gum arabic (5%) were orally administered (5 ml/kg), then, after 1, 2 and 4 hours, PAF was injected. The rate of inhibition of lowering of blood pressure after administration of the test samples against the control was evaluated.

The results are shown in Table 2.

TABLE 2

| No. of Working Example corresponding to test compound | Dosage (mg/kg) | Inhibitory Action on PAF-Induced Hypotension (%) | | |
|---|---|---|---|---|
| | | After 1 hr. | After 2 hrs. | After 4 hrs. |
| 3 | 30 | 86 | 63 | 26 |
| 4 | 30 | 64 | 32 | 22 |
| 5 | 30 | 91 | 93 | 88 |
| 12 | 30 | 65 | 40 | 24 |
| 22 | 30 | 94 | 80 | 2 |
| 23 | 30 | 94 | 94 | 67 |
| 24 | 30 | 94 | 91 | 78 |
| 25 | 30 | 100 | 97 | 70 |
| 26 | 30 | 98 | 99 | 100 |
| 26 | 10 | 100 | 100 | 87 |
| 26 | 3 | 74 | 70 | 44 |
| 27 | 30 | 100 | 100 | 86 |
| 27 | 10 | 79 | 75 | 62 |
| 28 | 30 | 92 | 91 | 92 |
| 29 | 30 | 100 | 100 | 100 |
| 29 | 3 | 67 | 71 | 61 |
| 33 | 30 | 99 | 99 | 79 |
| 7 | 30 | 4 | 15 | 25 |
| B | 30 | 86 | 63 | 26 |

TEST EXAMPLE 3

The rats were orally administered with a single dose each of the compound obtained in Working Example 7 and N,N'-bis(3,4,5-trimethoxybenzoyl)piperazine (1000 mg/kg). Observation was made with the passage of time for one week to confirm that all of the animals survived.

Accordingly, LD$_{50}$ values of the compound of the Working Example 7 and N,N'-bis(3,4,5-trimethoxybenzoyl)piperazine when orally administered to rats are estimated as 1000 mg/kg.

What is claimed is:

1. A compound of the formula (I) or a pharmaceutically acceptable salt thereof:

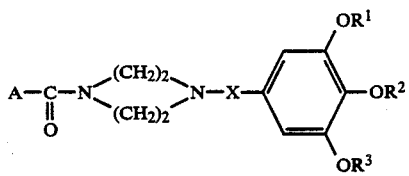

wherein A is a 2,3-dihydro-1-benzoxepin-4yl group unsubstituted or substituted by 1 to 4 members selected from the group consisting of a lower alkyl group, a halo lower alkyl group, a hydroxy lower alkyl group, a lower alkanoyloxy lower alkyl group, benzoyloxy lower alkyl group, a lower alkoxy-lower alkyl group, a lower alkoxy group, a halo lower alkoxy group, a lower alkoxy carbonyl-lower alkoxy group, a lower alkenyloxy group, phenyl lower alkyloxy group, a lower alkoxy-lower alkoxy group, a lower alkoxycarbonyl group, carboxyl group, carbamoyl group, an N,N-di-lower alkylcarbamoyl group, an N-lower alkyl carbamoyl group, halo group, cyano group, nitro group, hydroxy group, lower alkanoyloxy group, benzoyloxy group, amino group, a lower alkylsulfonylamino group, lower alkanoylamino group, benzoylamino group, a lower alkoxycarbonylamino group, a lower alkanoyl, benzoyl group, mercapto group, a lower alkylthio group, a lower alkylsulfinyl group and a lower alkylsulfonyl group; X is a methylene group, carbonyl group or thiocarbonyl group; and R$^1$, R$^2$ and R$^3$ are independently a lower alkyl group.

2. A compound according to claim 1, wherein A is a group of the formula:

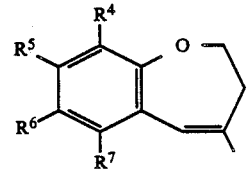

wherein R$^4$, R$^5$, R$^6$ and R$^7$ are independently hydrogen, a lower alkyl group, a halo lower alkyl group, a hydroxy lower alkyl group, a lower alkanoyloxy lower alkyl group, benzoyloxy lower alkyl group, a lower alkoxy-lower alkyl group, a lower alkoxy group, a halo lower alkoxy group, a lower alkoxy carbonyl-lower alkoxy group, a lower alkenyloxy group, phenyl lower alkyloxy group, a lower alkoxy-lower alkoxy group, a lower alkoxycarbonyl group, carboxyl group, carbamoyl group, an N,N-di-lower alkylcarbamoyl group, an N-lower alkyl carbamoyl group, halo group, cyano group, nitro group, hydroxy group, lower alkanoyloxy group, benzoyloxy group, amino group, a lower alkylsulfonylamino group, lower alkanoylamino group, benzoylamino group, a lower alkoxycarbonylamino group, a lower alkanoyl, benzoyl group, mercapto group, a lower alkylthio group, a lower alkylsulfinyl group or a lower alkylsulfonyl group.

3. A compound according to claim 2, wherein R$^4$, R$^5$, R$^6$ and R$^7$ are independently hydrogen, a lower alkyl group or a lower alkoxy group.

4. A compound according to claim 3, wherein R$^4$ and R$^7$ are hydrogen.

5. A compound according to claim 4, wherein R$^5$ and R$^6$ are a lower alkoxy group.

6. A compound according to claim 5, wherein a lower alkoxy group is methoxy group.

7. A compound according to claim 1, wherein X is carbonyl group.

8. A compound according to claim 1, wherein R$^1$, R$^2$ and R$^3$ are the same lower alkyl group.

9. A compound according to claim 1, wherein R$^1$, R$^2$ and R$^3$ are all methyl.

10. A compound according to claim 1, which is 1-(7,8-dimethoxy-2,3-dihydro-1-benzoxepin-4-carbonyl)-4-(3,4,5-trimethoxybenzyl)piperazine.

11. A compound according to claim 1, which is 1-(7,8-dimethoxy-2,3-dihydro-1-benzoxepin-4-carbonyl)-4-(3,4,5-trimethoxybenzoyl)piperazine.

12. A compound according to claim 1, which is 1-(7-methoxy-2,3-dihydro-1-benzoxepin-4-carbonyl)-4-(3,4,5trimethoxybenzoyl)piperazine.

13. A compound according to claim 1, which is 1-(7,8-dimethoxy-2,3-dihydro-1-benzoxepin-4-carbonyl)-4-(3,4,5-trimethoxybenzoyl)piperazine.

14. A platelet activating factor inhibiting composition which comprises
   (a) as the active ingredient, an effective platelet activating factor inhibiting amount of a compound as claimed in claim 1 or a pharmaceutically acceptable salt thereof and
   (b) a pharmaceutically acceptable carrier or excipient therefor.

* * * * *